(12) United States Patent
Frostegård et al.

(10) Patent No.: US 11,801,283 B2
(45) Date of Patent: Oct. 31, 2023

(54) THERAPEUTIC COMPOSITIONS

(71) Applicant: ANNEXIN PHARMACEUTICALS AB, Stockholm (SE)

(72) Inventors: Johan Frostegård, Stockholm (SE); Anna Frostegård, Stockholm (SE); Divya Thiagarajan, Stockholm (SE)

(73) Assignee: ANNEXIN PHARMACEUTICALS AB, Stockholm (SE)

( * ) Notice: Subject to any disclaimer, the term of this patent is extended or adjusted under 35 U.S.C. 154(b) by 75 days.

(21) Appl. No.: 16/484,657

(22) PCT Filed: Feb. 8, 2018

(86) PCT No.: PCT/EP2018/053230
§ 371 (c)(1),
(2) Date: Aug. 8, 2019

(87) PCT Pub. No.: WO2018/146228
PCT Pub. Date: Aug. 16, 2018

(65) Prior Publication Data
US 2019/0374604 A1    Dec. 12, 2019

(30) Foreign Application Priority Data
Feb. 9, 2017 (GB) .................................. 1702144

(51) Int. Cl.
*A61K 38/17* (2006.01)
*A61P 19/02* (2006.01)
*C07K 14/47* (2006.01)

(52) U.S. Cl.
CPC .......... *A61K 38/1709* (2013.01); *A61P 19/02* (2018.01); *C07K 14/47* (2013.01)

(58) Field of Classification Search
CPC ............................ A61K 38/17; A61P 19/02
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | Decant et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,596,556 A | 6/1986 | Morrow et al. | |
| 4,790,824 A | 12/1988 | Morrow et al. | |
| 4,941,880 A | 7/1990 | Burns | |
| 5,064,413 A | 11/1991 | McKinnon et al. | |
| 5,312,335 A | 5/1994 | McKinnon et al. | |
| 5,383,851 A | 1/1995 | McKinnon et al. | |
| 5,399,163 A | 3/1995 | Peterson et al. | |
| 9,192,649 B2 * | 11/2015 | Feng | A61P 9/00 |
| 10,060,908 B2 | 8/2018 | Frostegård | |
| 2003/0152513 A1 | 8/2003 | Blankenberg | |
| 2008/0044404 A1 | 2/2008 | Cederholm et al. | |
| 2011/0250208 A1 | 10/2011 | Frostegård | |
| 2012/0014920 A1 | 1/2012 | Feng et al. | |
| 2012/0094895 A1 | 4/2012 | Reutelingsperger | |
| 2014/0037614 A1 | 2/2014 | Pettersson | |
| 2014/0363450 A1 * | 12/2014 | Frostegård | A61P 25/00 435/7.92 |
| 2019/0086395 A1 | 3/2019 | Frostegård | |

FOREIGN PATENT DOCUMENTS

| | | |
|---|---|---|
| CN | 102256617 A | 11/2011 |
| WO | WO 00/035436 | 6/2000 |
| WO | WO 02/067857 | 9/2002 |
| WO | WO 2005/099744 | 10/2005 |
| WO | WO 2009/103977 | 8/2009 |
| WO | WO 2010/043045 A1 | 4/2010 |
| WO | WO 2010/069605 | 6/2010 |
| WO | WO 2011/160845 | 12/2011 |
| WO | WO 2014/197681 | 12/2014 |
| WO | WO-2014197681 A1 * | 12/2014 ............. A61P 29/00 |

OTHER PUBLICATIONS

Mukherjee et al., Nuclear Medicine and Biology, 2006, vol. 33(5):635-643.*
Tang et al., Int. J. Oncol., 2017, vol. 50(5):1839-1847.*
Fioravanti et al., Rheumatol. Int., 2009, vol. 29:961-965.*
Koutroumpas et al., Int. J. Biomed. Sci., 2013, vol. 9(4):217-223.*
Loeser et al., Arthritis Rheum., 2012, 64(6): 1697-1707.*
"Arthrex-ABPS Autologous Blood Processing System". Arthrex Vet Systems, München-Freiham, Germany, dated 2016.
"Osteoarthritis"—NHS Choices, accessed from http://www.nhs.uk/conditions/osteoarthritis/Pages/Introduction.aspx on Aug. 4, 2016.
"Osteoarthritis"—NHS Choices, accessed from http://www.nhs.uk/conditions/osteoarthritis/Pages/treatment.aspx on Aug. 4, 2016.
Basova LV et al: "Cardiolipin switch in mitochondria: shutting off the reduction of cytochrome c and turning on the peroxidase activity." *Biochemistry*. (2007) 46:3423-34.
Belikova NA et al: "Cardiolipin-specific peroxidase reactions of cytochrome C in mitochondria during irradiation-induced apoptosis." *Int J Radiat Oneal Biol Phvs*. (2007) 69: 176-86.
Benito, Maria J., et al. "Synovial tissue inflammation in early and late osteoarthritis." *Annals of the rheumatic diseases* 64.9 (2005): 1263-1267.
Bhadra et al. (2002). Pegnology: a review of PEG-ylated systems. Pharmazie. 57(1):5-29.
Bozic et al. (1997). Influence of degraded phosphatidylserine on binding of antiphospholipid antibodies. Int Arch Allergy Immunol. 112(1):19-26.
Brey, MD, et al., "β₂-Glycoprotein 1-Dependent Anticardiolipin Antibodies and Risk of Ischemic Stroke and Myocardial Infarction", 2001, pp. 1701-1706, vol. 32, Stroke.
Carmona and Prades, 2005, Compendium Equine: Continuing Education for Veterinarians.

(Continued)

*Primary Examiner* — Xiaozhen Xie
(74) *Attorney, Agent, or Firm* — Parker Highlander PLLC

(57) ABSTRACT

The invention relates to novel methods, uses and compositions for the prophylaxis or the treatment of osteoarthritis, and conditions associated therewith.

22 Claims, 5 Drawing Sheets

Specification includes a Sequence Listing.

(56) References Cited

OTHER PUBLICATIONS

Cederholm A et al: "Decreased binding of annexin v to endothelial cells—a potential mechanism in atherothrombosis of patients with systemic lupus erythematosus." *Arteriosclerosis, Thrombosis, And Vascular Biology*, Lippincott Williams & Wilkins, US. (Jan. 1, 2005) 25: 1: 198-203.

Cederholm, Anna, and Johan Frostegård. "Annexin A5 in cardiovascular disease and systemic lupus erythematosus." *Immunobiology* 210.10 (2005): 761-768.

Charlier et al. (2016). Insights on Molecular Mechanisms of Chondrocytes Death in Osteoarthritis. Int J Mol Sci. 17(12):2146.

Chauhan Abha et al: "Interaction of amyloid beta-protein with anionic phospholipids: Possible involvement of Lys28 and C-terminus aliphatic amino acids." *Neurochemical Research*, Plenum Press, New York, US LNG DOI:10.1023/A:1007509608440. (Mar. 1, 2000) 25:3:423-429.

Chicco AJ et al: "Role of cardiolipin alterations in mitochondrial dysfunction and disease." *Am J Physiol Cell Physiol.* (2007) 292:C33-44.

Chollet, MD, et al., "Annexin V-Coated Intraocular Lenses", 1996, pp. 818-824, vol. 22, J Cataract Refract Surg.

De Hooge, Alfons SK, et al. "Male IL-6 gene knock out mice developed more advanced osteoarthritis upon aging." *Osteoarthritis and cartilage* 13.1 (2005): 66-73.

De Rezende and de Campos "Is osteoarthritis a mechanical or inflammatory disease?." *Revista brasileira de ortopedia* 48.6 (2013): 471-474.

De Souza (2016). Osteoarthritis in horses—Part 1: relationship between clinical and radiographic examination for the diagnosis. Braz Arch Biol Technol. 59:e16150024.

Deguchi H et al: "Cardiolipin is a normal component of human plasma lipoproteins." *Proc Natl Acad Sci USA.* (2000) 97:1743-8.

Dubois, et al., "High Levels of Antibodies to Annexins V and VI in Patients with Rheumatoid Arthritis", 1995, pp. 1230-1234, vol. 22, No. 7, The Journal of Rheumatology.

Ea et al. (2008). Annexin 5 overexpression increased articular chondrocyte apoptosis induced by basic calcium phosphate crystals. Ann Rheum Dis. 67(11):1617-25. Epub Jan. 24, 2008.

European Office Action for EP 13 188 367.0-1408 dated Feb. 20, 2015.

Ewing et al. (2011). Annexin A5 therapy attenuates vascular inflammation and remodeling and improves endothelial function in mice. Arterioscler Thromb Vasc Biol. 31(1):95-101.

Experimental report in respect of European Patent Application No. 09796630.3, dated Mar. 31, 2017.

Febbraio M et al: "Targeted disruption of the class B scavenger receptor CD36 protects against atherosclerotic lesion development in mice. J Clin Invest." (2000) 105: 1049-56.

Frostegård (2010). Low level natural antibodies against phosphorylcholine: a novel risk marker and potential mechanism in atherosclerosis and cardiovascular disease. Clin Immunol. 134(1):47-54. Epub Sep. 11, 2009.

Frostegard J et al: "Cytokine expression in advanced human atherosclerotic plaques: dominance of pro-inflammatory (Th1) and macrophage stimulating cytokines." *Atherosclerosis.* (1999) 145:33-43.

Frostegard J: "Atherosclerosis in patients with autoimmune disorders." *Arterioscler Thromb Vasc Biol.* (2005) 25: 1776-85.

Frostegard Johan et al: "Lipid peroxidation is enhanced in patients with systemic lupus erythematosus and is associated with arterial and renal disease manifestations." *Arthritis & Rheumatism.* (Jan. 2005) 52: 1: 192-200.

Funk CD: "Leukotriene modifiers as potential therapeutics for cardiovascular disease." *Nat Rev Drug Discov.* (2005) 4:664-72.

Gonzalvez Fetal: "Cardiolipin: setting the beat of apoptosis." *Apoptosis.* (2007) 12:877-85.

Goodarzi K et al: "Leukotriene 84 and BL T1 control cytotoxic effector T cell recruitment to inflamed tissues." *Nat Immunol.* (2003) 4:965-73.

Griffiths, R. J., et al. "Leukotriene B4 plays a critical role in the progression of collagen-induced arthritis." Proceedings of the National Academy of Sciences 92.2 (1995): 517-521.

Hamsten A et al: "Antibodies to cardiolipin in young survivors of myocardial infarction: an association with recurrent cardiovascular events." *Lancet.* (1986) 1 :113-6.

Han X et al: "Alterations in myocardial cardiolipin content and composition occur at the very earliest stages of diabetes: a shotgun lipidomics study." *Biochemistry.* (2007) 46:6417-28.

Hansson GK: "Inflammation, atherosclerosis, and coronary artery disease." *N Engl J Med.* (2005) 352: 1685-95.

Harris et al. (2001). Pegylation: a novel process for modifying pharmacokinetics. Clin Pharmacokinet. 40(7):539-51.

Hiligsmann & Reginster (2013). The economic weight of osteoarthritis in Europe. Medicographia. 35(2):197-202.

Horkko S et al: "Antiphospholipid antibodies are directed against epitopes of oxidized phospholipids. Recognition of cardiolipin by monoclonal antibodies to epitopes of oxidized low density lipoprotein." *The Journal of Clinical Investigation* Aug. 1, 1996. (Aug. 1, 1996) 98:3:815-825.

House and Morton. "Interleukin-1 Receptor Antagonist Protein (IRAP®) Therapy for Equine Osteoarthritis". College of Veterinary Medicine, University of Florida, Gainesville, FL, accessed from http://extension.vetmed.ufl.edu/files/2011/10/IRAPFinal.pdf, dated 2011.

International Preliminary Report on Patentability for PCT /EP2009/009199, dated Jun. 19, 2011.

International Search Report for PCT/EP2009/009199, dated Oct. 4, 2010.

Ishii H et al: "Recombinant Annexin-2 inhibits the progress of diabetic nephropathy in a diabetic mouse model via recovery of hypercoagulability." *Thromb Haemost.* (2007) 97:124-8.

Kim & Kirsch (2008). Collagen/annexin V interactions regulate chondrocyte mineralization, J Biol Chem. 283(16):10310-7, Epub Feb. 14, 2008.

Kirsch et al. (2000). Activation of annexin II and V expression, terminal differentiation, mineralization and apoptosis in human osteoarthritic cartilage. Osteoarthritis Cartilage. 8(4):294-302.

Klimiuk, PA1, et al. "Soluble adhesion molecules (ICAM-1, VCAM-1, and E-selectin) and vascular endothelial growth factor (VEGF) in patients with distinct variants of rheumatoid synovitis." *Annals of the rheumatic diseases* 61.9 (2002): 804-809.

Komori (2016). Cell Death in Chondrocytes, Osteoblasts, and Osteocytes. Int J Mol Sci. 17(12):2045.

Kozlowski & Harris (2001). Improvements in protein PEGylation: pegylated interferons for treatment of hepatitis C. J Control Release. 72(1-3):217-24.

Kozlowski et al. (2001). Development of pegylated interferons for the treatment of chronic hepatitis C. BioDrugs. 15(7):419-29.

Lee et al. (2002). Annexin 5 and apolipoprotein E2 protect against Alzheimer's amyloid-beta-peptide cytotoxicity by competitive inhibition at a common phosphatidylserine interaction site. Peptides. 23(7):1249-63.

Levine, Steven R., et al. "Ischemic stroke associated with anticardiolipin antibodies." *Stroke* 18.6 (1987): 1101-1106.

Lipsky, Peter E. "Interleukin-6 and rheumatic diseases." *Arthritis Research & Therapy* 8.S2 (2006): S4.

Lorberboym et al. (2009). The use of 99mTc-recombinant human annexin V imaging for differential diagnosis of aseptic loosening and low-grade infection in hip and knee prostheses. J Nucl Med. 50(4):534-7. Epub Mar. 16, 2009.

Luong et al. (2001). Seasonal distribution of antiphospholipid antibodies. Stroke. 32(8):1707-11.

Mabey & Honsawek (2015). Cytokines as biochemical markers for knee osteoarthritis. World J Orthop. 6(1):95-105.

Martin W et al: "An overview of endosymbiotic models for the origins of eukaryotes, their ATP-producing organelles (mitochondria and hydrogenosomes), and their heterotrophic lifestyle." *Biol Chem.* (2001) 382:1521-39.

McCoy (2015). Animal models of osteoarthritis: comparisons and key considerations. Vet Path. 52(5):803-18.

McIlwraith et al. (2012). The horse as a model of naturally occurring osteoarthritis. Bone Joint Res. 1(11):297-309.

(56) References Cited

OTHER PUBLICATIONS

Mirsaeidi, Mehdi, et al. "Annexins family: insights into their functions and potential role in pathogenesis of sarcoidosis." *Journal of translational medicine* 14.1 (2016): 89.

Moore KJ et al: "Scavenger receptors in atherosclerosis: beyond lipid uptake." *Arterioscler Thromb Vase Biol.* (2006) 26:1702-11.

Munoz et al. (2007). The role of annexin A5 in the modulation of the immune response against dying and dead cells. Curr Med Chem. 14(3):271-7.

Nakagawa Y: "Initiation of apoptotic signal by the peroxidation of cardiolipin of mitochondria." *Ann N YAcad Sci.* (2004) 1011:177-84.

Pierangeli et al. (1994). Effect of human IgG antiphospholipid antibodies on an in vivo thrombosis model in mice. Thromb Haemost. 71(5):670-4.

Pierangeli, et al., "Antiphospholipid Antibodies in an in vivo Thrombosis Model in Mice", 1994, pp. 247-251, vol. 3, Lupus.

Pope S et al: "Oxidative stress and mitochondrial dysfunction in neurodegeneration; cardiolipin a critical target?" *Biochimica et Biophysica Acta.—Bioenergetics*, Amsterdam, NL LNKD 001:10.1016/J.BBABI0.2008.03.011. (Jul. 1, 2008) 1777:7-8:794-799.

Post, Anneke M., et al. "Imaging cell death with radiolabeled annexin V in an experimental model of rheumatoid arthritis." *Journal of Nuclear Medicine* 43.10 (2002): 1359-1365.

Pratico Domenico et al: "Circulating autoantibodies to oxidized cardiolipin correlate with isoprostane F2alpha-VI, levels and the extent of atherosclerosis in ApoE-deficient mice: Modulation by vitamin E." *Blood.* (Jan. 15, 2001) 97:2, 15:459-464.

Qiu H et al: "Expression of 5-lipoxygenase and leukotriene A4 hydrolase in human atherosclerotic lesions correlates with symptoms of plaque instability." *Proc Natl Acad Sci USA.* (2006) 103:8161-6.

Rand JH et al: "Antibody-mediated disruption of the annexin-V antithrombotic shield: a new mechanism for thrombosis in the antiphospholipid syndrome." *Thromb Haemost.* (1999) 82:649-55.

Reddy (2000). Controlled-release, pegylation, liposomal formulations: new mechanisms in the delivery of injectable drugs. Ann Pharmacother, 34(7-8):915-23.

Reutelingsperger, et al., "Annexin V, the Regulator of Phosphatidylserine-Catalyzed Inflammation and Coagulation during Apoptosis", 1997, pp. 527-532, vol. 53, CMLS Cellular and Molecular Life Sciences.

Roberts et al. (2002). Chemistry for peptide and protein PEGylation. Adv Drug Deliv Rev. 54(4):459-76.

Rodriguez-Garcia, et al., "Annexin V Autoantibodies in Rheumatoid Arthritis", 1996, pp. 895-900, vol. 55, Ann Rheum Dis.

Ross et al. (2012). Evaluation of the inflammatory response in experimentally induced synovitis in the horse: a comparison of recombinant equine interleukin 1 beta and lipopolysaccharide. Osteoarthritis Cartilage. 20(12):1583-90. Epub Aug. 21, 2012.

Schlame M et al: "Effect of cardiolipin oxidation on solid-phase immunoassay for antiphospholipid antibodies." *Thrombosis and Haemostasis*, SchattauerGmbh, De; Us. (Dec. 1, 2001) 86:6:1475-1482.

Schlame M et al: "The biosynthesis and functional role of cardiolipin." *Prog Lipid Res.* (2000) 39:257-88.

Schlame M: "Cardiolipin synthesis for the assembly of bacterial and mitochondrial membranes." *J Lipid Res.* (2008) 49:1607-20.

Schlame Met Al: "Deficiency of tetralinoleoyl-cardiolipin in Barth syndrome." *Ann Neurol.* (2002) 51 :634-7.

Serezani CH et al: "Leukotrienes enhance the bactericidal activity of alveolar macrophages against Klebsiella pneumoniae through the activation of NADPH oxidase." *Blood.* (2005) 106:1067-75.

Sjoberg BG et al: "Low levels of IgM antibodies against phosphorylcholine—a potential risk marker for ischemic stroke in men", *Atherosclerosis.* (2008) 203: 528-532.

Sparagna GC et al: "Loss of cardiac tetralinoleoyl cardiolipin in human and experimental heart failure." *J Lipid Res.* (2007) 48:1559-70.

Stegnar et al. (1991). Prevalence of antiphospholipid antibodies in deep vein thrombosis and their relationship to blood coagulation and fibrinolysis. Thromb Res. 63(4):433-43.

Szekanecz, Zoltan, et al. "Differential Distribution of Intercellular Adhesion Molecules (ICAM-1, ICAM-2, and ICAM-3) and the MS-1 Antigen in Normal and Diseased Human Synovia." *Arthritis & Rheumatism: Official Journal of the American College of Rheumatology* 37.2 (1994): 221-231.

Thiagarajan P et al: "Inhibition of arterial thrombosis by recombinant annexin Vin a rabbit carotid artery injury model." *Circulation.* (1997) 96:2339-47.

Tuhrim et al. (1999). Antiphosphatidyl serine antibodies are independently associated with ischemic stroke. Neurology. 53(7):1523-7.

Tuominen, Anu, et al. "A natural antibody to oxidized cardiolipin binds to oxidized low-density lipoprotein, apoptotic cells, and atherosclerotic lesions." *Arteriosclerosis, thrombosis, and vascular biology* 26.9 (2006): 2096-2102.

Vaarala 0 et al: "Cross reaction between antibodies to oxidised low-density lipoprotein and to cardiolipin in systemic lupus erythematosus." *Lancet.* (1993) 341 :923-5.

Vaarala Outi et al: "Anti-cardiolipin antibodies and risk of myocardial infarction in a prospective cohort of middle-aged men," *Circulation.* (1995) 91: 1 :23-27.

Vaarala, et al., "Anticardiolipin Response in Acute Infections", 1986, pp. 8-15, vol. 41, Clinical Immunology and Immunopathology.

Vay et al. (2006). Anti-phospholipid antibodies associated with alcoholic liver disease target oxidized phosphatidylserine on apoptotic cell plasma membranes. J Hepatol. 44(1):183-9. Epub Jul. 11, 2005.

Vermes et al. (1995). A novel assay for apoptosis. Flow cytometric detection of phosphatidylserine expression on early apoptotic cells using fluorescein labelled Annexin V. J Immunol Methods. 184(1):39-51.

Veronese (2001). Peptide and protein PEGylation: a review of problems and solutions. Biomaterials. 22(5):405-17.

Von Landenberg et al. (2003). The combination of different antiphospholipid antibody subgroups in the sera of patients with autoimmune diseases is a strong predictor for thrombosis. A retrospective study from a single center. Immunobiology. 207(1):65-71.

Wan (2010). Studies on leukotriene B4 and alarmins in inflammatory responses. Ph.D. Thesis, Department of Medical Biochemistry and Biophysics, Karolinska Institutet, Stockholm, Sweden, Jan. 29, 2010.

Wan et al. (2014). Oxidized but not native cardiolipin has pro-inflammatory effects, which are inhibited by Annexin A5. Atherosclerosis. 235(2):592-8.

Wan Met Al: "Leukotriene B4 triggers release of the cathelicidin LL-37 from human neutrophils: novel lipid-peptide interactions in innate immune responses." *Faseb j.* (2007) 21 :2897-905.

Weissmann, Gerald, and Helen Korchak. "Rheumatoid arthritis." *Inflammation* 8.1 (1984): S3-S14.

Winyard PG et al: "Presence of foam cells containing oxidised low density lipoprotein in the synovial membrane from patients with rheumatoid arthritis." *Ann Rheum Dis.* (1993) 52:677-80.

Wolf, P., et al. "Anticardiolipin antibodies in rheumatoid arthritis: their relation to rheumatoid nodules and cutaneous vascular manifestations." *British Journal of Dermatology* 131.1 (1994): 48-51.

Written Opinion of the International Searching Authority for PCT/EP2009/009199, dated Jun. 19, 2011.

Wu, et al., "Antibodies Against Cardiolipin and Ocidatively Modified LDL in 50-Year-Old-Men Predict Myocardial Infarction", 1997, pp. 3159-3163, vol. 17, Arteriosclerosis, Thrombosis and Vascular Biology, doi:10.1161/01.ATV.17.11.3159.

Yin, et al., "Free Radical Oxidation of Cardiolipin: Chemical Mechanisms, Detection and Implication in Apoptosis, Mitochondrial Dysfunction and Human Diseases", Jan. 1, 2012, pp. 1-16, Free Radical Research, XP007922100.

Yokomizo T et al: "A G-protein-coupled receptor for leukotriene 84 that mediates chemotaxis." *Nature.* (1997) 387:620-4.

Yokomizo T et al: "A second leukotriene 8(4) receptor, BL T2. A new therapeutic target in inflammation and immunological disorders." *J Exp Med.* (2000) 192:421-32.

(56) References Cited

OTHER PUBLICATIONS

Zhou X et al: "LDL immunization induces T-cell-dependent antibody formation and protection against atherosclerosis." *Arteriosclerosis, Thrombosis, And VascularBioloav*Jan. 2001. (Jan. 2001) 21:1:108-114.
Song et al., 2008, 3 pages (no English translation avalable).
Wei Yusuo, 2016, 4 pages (no English translation available).

* cited by examiner

THERAPEUTIC COMPOSITIONS

This application is a national phase application under 35 U.S.C. § 371 of International Application No. PCT/EP2018/053230, filed Feb. 8, 2018, which claims priority to United Kingdom Application No. 1702144.5, filed Feb. 9, 2017. The entire text of each of the above referenced disclosures is specifically incorporated herein by reference.

FIELD OF THE INVENTION

The invention relates to novel methods, uses and compositions for the prophylaxis or the treatment of osteoarthritis, and conditions associated therewith.

BACKGROUND TO THE INVENTION

The listing or discussion of an apparently prior-published document in this specification should not necessarily be taken as an acknowledgement that the document is part of the state of the art or is common general knowledge.

Osteoarthritis is a chronic degenerative disease which is prevalent in the worldwide population, causing pain and stiffness in the joints of the patient. The prevalence of the disease leads to a large economic burden on society due to the cost of patient care and loss of an individual's productivity (Hiligsmann and Reginster 2013, Medicographia, 35: 197-202).

Generally, osteoarthritis is considered to be a disease caused by the use of the joint (for example, general "wear and tear"). Such a physical causation of osteoarthritis explains why the disease is commonplace in older subjects, and why common risk factors are being overweight and having a profession in which joints are put under stress. However, some research indicates that the onset and progression of osteoarthritis has an inflammatory component. This has led to an ongoing dispute in the field of medicine as to what are the pathophysiological causes of osteoarthritis (Uchôa de Rezende and Constantino de Campos 2013, Rev. Bras. Ortop. 48(6):471-474).

As well as affecting human subjects, osteoarthritis is also a disease which affects animals. For example, in horses, osteoarthritis is estimated to be the cause of approximately 60% of lameness (McIlwraith et al., 2012 Bone Joint Res., 1: 297-309).

Currently, there is no cure for osteoarthritis, either in human or animal patients. Patients are provided with medication to manage symptoms (for example, pain medication, such as paracetamol), and in some cases surgery to replace the affected joint (for example, a hip replacement).

There is, therefore, a need for new prophylactic and therapeutic treatments for osteoarthritis.

Annexin A5 is a protein which, amongst other properties, binds phosphatidylserine. It is generally considered to be therapeutically valuable for treating cardiovascular diseases, such as restenosis and atherosclerosis (WO 2009/103977 and WO 2005/099744).

Previously, research had suggested that Annexin A5 is involved in processes which worsen osteoarthritis. In healthy joints and tissues, chondrocytes (specifically, articular chondrocytes) have a role for producing, maintaining, remodelling and repairing the extracellular matrix of articular cartilage, including regulating mineralisation and calcification of the extracellular matrix. Regions of the joint in which no calcification occurs are called "mineralisation restricted sites". Within that normal tissue, the process of mineralisation is undertaken by differentiated articular chondrocytes deep within the cartilage. The chondrocyte differentiation and the subsequent extracellular mineralisation is mediated by the chondrocytes expressing Annexin A5 and releasing mineralisation-competent vesicles. Via binding with type II and type X collagen, Annexin A5 anchors the vesicles to the extracellular matrix. Annexin A5 also forms calcium ion ($Ca^{2+}$) channels in the vesicles allowing for the rapid movement of those ions, initiating the process of mineralisation and calcification (Kim and Kirsch 2008, The Journal of Biological Chemistry, 283(16): 10310-10317).

In joints and tissues with osteoarthritis, it was previously observed that chondrocyte differentiation and extracellular mineralisation mediated by cell-surface Annexin A5 and extracellular vesicles occurs throughout the joint, rather than just deep within the cartilage.

This ectopic chondrocyte differentiation was reported to lead to chondrocyte cell death, whilst the upregulated expression of Annexin A5 mineralisation in chondrocytes was reported to lead to mineral deposits arising inappropriately throughout the joint. It is thought that the mineralisation and calcification causes subsequent inflammation and destruction of the joint tissue, which is implicated in the contribution to the initiation and development of osteoarthritis (Kirsch et al., 2000, Osteoarthritis and Cartilage, 8: 294-302).

Accordingly, to the extent that Annexin A5 had previously been directly studied in the context of osteoarthritis, it had been considered to contribute to the development of osteoarthritis.

Surprisingly, against this background, the inventors have now identified that Annexin A5 protein can be used for the prophylaxis or the treatment of osteoarthritis, and in particular osteoarthritis caused by inflammation. Although this work is applicable to osteoarthritis in any subject, the inventors show that it is particularly applicable to osteoarthritis in both humans and horses.

Accordingly, the object of the present invention is to provide a therapeutic agent for the prophylaxis or the treatment of osteoarthritis, and conditions associated therewith.

SUMMARY OF THE INVENTION

The present invention is based on the applicant's surprising finding that Annexin A5 protein can be used in the treatment and prophylaxis of osteoarthritis, and one or more conditions associated therewith.

In a first aspect, the present invention provides Annexin A5 protein for use in the prophylaxis or the treatment of osteoarthritis, or a condition associated therewith, in one or more joints, in a subject;
  wherein the or each joint is selected from the list consisting of: a synovial joint; an amphiarthrosis joint; and a synarthrosis joint.

In an alternative embodiment of the first aspect, the present invention provides a method for the prophylaxis or the treatment of osteoarthritis, or a condition associated therewith, in one or more joints, in a subject;
  wherein the or each joint is selected from the list consisting of: a synovial joint; an amphiarthrosis joint; and a synarthrosis joint;
  and wherein the method comprises the step of administering a therapeutically effective amount of the Annexin A5 protein to the subject.

In another alternative embodiment of the first aspect, the present invention provides for the use of Annexin A5 protein in the manufacture of a medicament for the prophylaxis or the treatment of osteoarthritis, or a condition associated therewith, one or more joints, in a subject;
wherein the or each joint is selected from the list consisting of: a synovial joint; an amphiarthrosis joint; and a synarthrosis joint.

In a second aspect, the present invention provides Annexin A5 protein for use in the prophylaxis or the treatment of osteoarthritis, or a condition associated therewith, in a subject.

In an alternative embodiment of the second aspect, the present invention provides a method for the prophylaxis or the treatment of osteoarthritis, or a condition associated therewith, in a subject;
wherein the method comprises the step of administering a therapeutically effective amount of the Annexin A5 protein to the subject.

In another alternative embodiment of the second aspect, the present invention provides for the use of Annexin A5 protein in the manufacture of a medicament for the prophylaxis or the treatment of osteoarthritis, or a condition associated therewith, in a subject.

In a third aspect, the present invention provides Annexin A5 protein for use in the prophylaxis or the treatment of osteoarthritis, or a condition associated therewith, in a joint, in a subject;
wherein the Annexin A5 protein is administered to the or each joint.

In an alternative embodiment of the third aspect, the present invention provides a method for the prophylaxis or the treatment of osteoarthritis, or a condition associated therewith, in a joint, in a subject;
wherein the Annexin A5 protein is administered to the or each joint;
and wherein the method comprises the step of administering a therapeutically effective amount of the Annexin A5 protein to the subject.

In another alternative embodiment of the third aspect, the present invention provides for the use of Annexin A5 protein in the manufacture of a medicament for the prophylaxis or the treatment of osteoarthritis, or a condition associated therewith, in a joint, in a subject;
wherein the Annexin A5 protein is administered to the or each joint.

In a fourth aspect, the present invention provides Annexin A5 protein for use in the prophylaxis or the treatment of erosive osteoarthritis, or a condition associated therewith, in a joint, in a subject.

In an alternative embodiment of the fourth aspect, the present invention provides a method for the prophylaxis or the treatment of erosive osteoarthritis, or a condition associated therewith, in a joint, in a subject;
wherein the method comprises the step of administering a therapeutically effective amount of the Annexin A5 protein to the subject.

In another alternative embodiment of the fourth aspect, the present invention provides for the use of Annexin A5 protein in the manufacture of a medicament for the prophylaxis or the treatment of erosive osteoarthritis, or a condition associated therewith, in a joint, in a subject.

In one embodiment, in accordance with the first, second or fourth aspects of the present invention, the Annexin A5 protein may optionally be administered to the or each joint.

In one embodiment, in accordance with the second, third or fourth aspects of the present invention, the or each joint may optionally be selected from the list consisting of: a synovial joint; an amphiarthrosis joint; and a synarthrosis joint.

In one embodiment, in accordance with the first, second or third aspects of the present invention, the osteoarthritis may optionally be primary osteoarthritis or secondary osteoarthritis.

In one embodiment, in accordance with the first, second or third aspects of the present invention, the primary osteoarthritis may optionally be generalised nodal osteoarthritis or erosive osteoarthritis.

In one embodiment, in accordance with any of the foregoing aspects of the present invention, the subject may have osteoarthritis in the or each joint.

In one embodiment, in accordance with any of the foregoing aspects of the present invention, the subject may optionally have been diagnosed with osteoarthritis;
optionally, the diagnosis of the osteoarthritis is in the or each joint to be treated.

In accordance with any of the foregoing aspects of the present invention, optionally the synovial joint is one or more synovial joint selected from the list consisting of: a plane joint (for example, a costovertebral joint, a facet joint, a midcarpal joint, a carpometacarpal finger joint, an intermetacarpal joint, a sacroiliac joint, a zygapophyseal joint, a sternocostal joint, subtalar joint (or talocalcaneal joint), or an acromioclavicular joint); a ball and socket joint (for example, a tibiotarsal joint, a tibiofibular joint, a shoulder joint, a talocalcaneonavicular joint, or a hip joint); a hinge joint (for example, an ankle joint, an elbow joint, a temporomandibular joint, an interphalangeal joint, a stifle joint, or a knee joint); a pivot joint (for example, an atlantoaxial joint, an atlanto-axial joint, a proximal radioulnar joint, a hock joint, a tarsal joint, a talocalcaneonavicular joint, a calcaneocuboid joint, or a distal radioulnar joint); a condyloid joint (for example, an atlanto-occipital joint, a radiocarpal joint, a metatarsophalangeal joint, a wrist joint, an intercarpal joint, a radiocarpal joint, or a metacarpophalangeal joint); and a saddle joint (for example, a carpometacarpal thumb joint, a calcaneocuboid joint, or a sternoclavicular joint).

In one embodiment, in accordance with any of the foregoing aspects of the present invention, the subject may optionally not be a juvenile and/or will have completed physical growth at the time of the prophylaxis or treatment.

In one embodiment, in accordance with any of the foregoing aspects of the present invention, the subject may optionally be a mammalian subject, such as a mammal selected from the group consisting of a human, an equine (including a horse), a bovine, a camel, a pig, a llama, an alpaca, a sheep, a goat, a canine, a feline, a rabbit, or a rodent. In one preferred option, the subject is a human. In another preferred option, the subject is a horse.

In one embodiment, in accordance with any of the foregoing aspects of the present invention, wherein the subject is a human the subject may be 45 or more years of age, such as an age as discussed further below in section D of the Detailed Description of the Invention, in this application.

In one embodiment, in accordance with any of the foregoing aspects of the present invention, wherein the subject is a horse the subject may be 5 or more years of age, such as an age as discussed further below in section D of the Detailed Description of the Invention, in this application.

In one embodiment, in accordance with any of the foregoing aspects of the present invention, the Annexin A5 protein may be administered at a concentration of at least 1 µg/ml.

In one embodiment, in accordance with any of the foregoing aspects of the present invention, the Annexin A5 protein may be:

a) a protein comprising, consisting essentially of, or consisting of the sequence of human Annexin A5 (optionally, a protein consisting of the sequence of SEQ ID NO:1, either with or without the N-terminal methionine);

b) a mammalian orthologue of human Annexin A5;

c) an allelic or genetic variant of a) or b);

d) a functional analogue or variant of Annexin which is a protein which is more than 50%, 60%, 70%, 75%, such as more than 80%, 85%, more than 90%, or even more preferably more than 95% or 99% identical to human Annexin A5, SEQ ID NO:1 either with, or without, the N-terminal methionine;

e) a biologically active fragment of any of a), b), c), or d);

f) a monomer consisting of, dimer comprising or consisting of, or a fusion protein comprising, any of a), b), c), d) or e); and g) a PEGylated variant of any of a), b), c), d), e) or f).

In one embodiment, in accordance with any of the foregoing aspects of the present invention, the Annexin A5 protein may be formulated in a composition, such as a pharmaceutically acceptable composition or a veterinarially acceptable composition.

In one embodiment, in accordance with any of the foregoing aspects of the present invention, the Annexin A5 protein or composition may be administered into the or each joint at a volume of 1 ml or more;

optionally, wherein the Annexin A5 protein or composition may be administered into the or each joint at a volume of 10 ml or less.

In one embodiment, in accordance with any of the foregoing aspects of the present invention, the subject may be treated with Annexin A5 protein or composition separately, simultaneously or sequentially with one or more additional treatments, selected from one or more of: lifestyle changes; medication; and surgery.

Further details of these, and other, aspects of the present invention, and the embodiments and options related thereto, are discussed further below in the Detailed Description of the Invention.

DEFINITIONS

Figure 1:
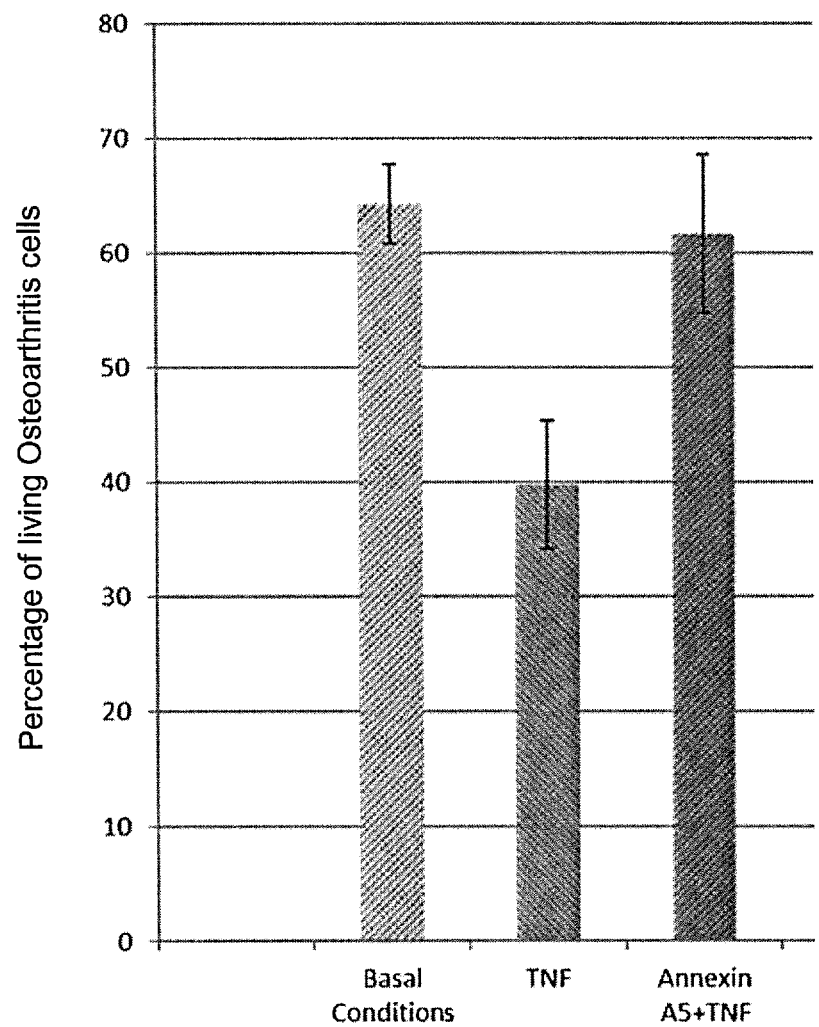
FIG. 1 shows that cell viability is increased in osteoarthritic cells on treatment with Annexin A5 protein. The experiment has been undertaken on a primary chondrocyte cell culture from an osteoarthritis patient using flow cytometry. The osteoarthritis joint inflammation was mimicked in the cells through the application of TNFα, which led to a reduction in cell viability (column two) when compared to control cells to which TNFα had not been applied (column one). Application of Annexin A5 in addition to TNFα inhibits cell death (column three), leading to a cell viability equivalent to levels seen in the control.

The term "Annexin A5 protein" as used herein is defined further below in section C of the detailed description of the invention. It optionally further includes the meaning of a composition comprising the Annexin A5 protein. Said composition may, for example, be a pharmaceutically acceptable, or veterinarially acceptable, composition.

A "pharmaceutically acceptable" composition may be a composition that is safe for administration to a subject, such as a human subject, by injection, such as intravenous, subcutaneous or intramuscular injection. In a particular embodiment, the pharmaceutically acceptable composition may be a composition that is safe for administration to the joint of the subject, such as a human subject, for example by injection into the joint cavity and/or into the synovial fluid of the joint. For example, in one optional embodiment, the composition comprises hyaluronic acid. The Annexin A5 protein may be present in a pharmaceutically acceptable composition that is formulated for injection into the joint cavity and/or into the synovial fluid of the joint in an amount and concentration suitable to deliver a prophylactically or therapeutically effective amount of Annexin A5 to the joint in a volume that is safely injected into the joint. Suitable volumes can be readily determined by the skilled person, and exemplary volumes are discussed below in section E of this application, and may for example range from 0.1 to 40 mL depending on the identity of the joint and the nature (species, gender, age, size, weight etc.) of the subject.

A "veterinarially acceptable" composition may be a composition that is safe for administration to an animal subject, such as by injection, for example by intravenous, subcutaneous or intramuscular injection. In a particular embodiment, the veterinarially acceptable composition may be a composition that is safe for administration to the joint of the animal subject, such as a horse, for example by injection into the joint cavity and/or into the synovial fluid of the joint. For example, in one optional embodiment, the composition comprises hyaluronic acid. The Annexin A5 protein may be present in a veterinarially acceptable composition that is formulated for injection into the joint cavity and/or into the synovial fluid of the joint in an amount and concentration suitable to deliver a prophylactically or therapeutically effective amount of Annexin A5 to the joint in a volume that is safely injected into the joint. Suitable volumes can be readily determined by the skilled person, and exemplary volumes are discussed below in section E of this application, and may for example range from 0.1 to 40 mL depending on the identity of the joint and the nature (species, gender, age, size, weight etc.) of the subject.

A pharmaceutical composition, or veterinary composition, according to the invention may thus comprise the Annexin A5 protein in admixture with a pharmaceutically or veterinarially acceptable adjuvant, diluent or carrier, which will typically be selected with regard to the intended route of administration and standard pharmaceutical practice. The composition may be in the form of immediate-, delayed- or controlled-release applications. The formulation may be a unit dosage containing a daily dose or unit, daily sub-dose or an appropriate fraction thereof, of the active ingredient.

The phrases "pharmaceutically acceptable", "pharmacologically acceptable" and "veterinarially acceptable" refer to compositions that do not produce an adverse, allergic or other untoward reaction when administered to an animal, such as, for example, a human, as appropriate. The preparation of such pharmaceutical compositions are known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards, such as those as required by FDA Office of Biological Standards.

As used herein, "pharmaceutically acceptable carrier" and "veterinarially acceptable carrier" include any and all solvents, dispersion media, coatings, surfactants, antioxidants, preservatives (e.g., antibacterial agents, antifungal agents), isotonic agents, salts, preservatives, drugs, drug stabilizers, excipients, disintegration agents, such like materials and combinations thereof, as would be known to one of ordinary skill in the art. Except insofar as any conventional carrier is incompatible with the active ingredient, its use in the therapeutic or pharmaceutical compositions is contemplated.

The Annexin A5 protein, or a pharmaceutically acceptable, or veterinarially acceptable, composition comprising the Annexin A5 protein can, for example, be administered parenterally, for example, intravenously, intra-arterially, intraperitoneally, intrathecally, intraventricularly, intrasternally, intracranially, intra-muscularly or subcutaneously, or may be administered by infusion techniques. Injection into the joint cavity and/or into the synovial fluid of the joint maybe of particular interest for the practice of the present invention, although it is not limited to these options. It may be used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration typically include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In one embodiment, the pharmaceutically acceptable, or veterinarially acceptable, composition may be defined as being safe for injection if it contains no, or substantially no, endotoxin. Endotoxin is often used synonymously with the term lipopolysaccharide, which is a major constituent of the outer cell wall of Gram-negative bacteria. It consists of a polysaccharide (sugar) chain and a lipid moiety, known as lipid A, which is responsible for the toxic effects observed with endotoxin. The polysaccharide chain is highly variable among different bacteria and determines the serotype of the endotoxin and the lipid components are also highly variable such that a single endotoxin sample may contain 10's to 100's of distinct molecular species. Endotoxin is approximately 10 kDa in size but can form large aggregates up to 1000 kDa. Endotoxin is typically harmful and pyrogenic in therapeutic compositions and regulatory authorities have imposed strict limitations on the allowable levels of endotoxin within a pharmaceutical composition. Accordingly, the level of endotoxin in a composition according to the second aspect of the present invention should be minimised and may be less than 100 endotoxin units (EU) per dose, such as less than 90, 80, 70, 60, 50 40, 30, 20, 10, 5, 4, 3, 2, 1 or less EU per dose. The concentration of endotoxin in a composition according to the second aspect of the present invention may be less than 200 EU/m3, such as less than 150, 100, 90, 80, 70, 60, 50 40, 30, 20, 10, 5, 4, 3, 2, 1 or less EU/m3. Methods for measuring endotoxin levels, such as the limulus amoebocyte assay (LAL) method, are well known in the art.

A composition comprising the Annexin A5 protein may optionally comprise the Annexin A5 protein as the sole active agent. For example, it may optionally exclude compositions in which Annexin A5 is formulated with, conjugated to, or expressed as a fusion protein with, one or more further protein or non-protein agents that are capable of providing an additional therapeutic effect. Said additional therapeutic effect may either be in the context of osteoarthritis or in the context of a therapeutic effect that is not relevant to osteoarthritis treatment.

Other Definitions

The term "treatment" would be understood by those skilled in medicine. The term "treatment" as used herein may include any treatment of a condition, (for example, wherein the condition is osteoarthritis), in a subject, particularly a human or other mammal (such as a horse), and optionally includes one or more of the following effects:
(i) inhibiting the condition (for example, osteoarthritis), i.e., slowing, reducing or arresting the development of the condition;
(ii) relieving the condition (for example, osteoarthritis), i.e., causing regression of the condition in a subject having the condition; or
(iii) curing the condition (for example, osteoarthritis), i.e. returning a subject having the condition, to a state of health in which the condition, is no longer detectable.

The term "prophylaxis" would be understood by those skilled in medicine. The term "prophylaxis" as used herein may include any prophylactic treatment of a condition (for example, wherein the condition is osteoarthritis) in a subject, particularly a human or other mammal (such as a horse), and optionally includes one or more of the following effects:
(i) preventing the condition (for example, osteoarthritis) from occurring in a subject (for example, a subject which may be predisposed to, or at risk of, developing the condition, but has not yet been diagnosed as having it) i.e. stopping the subject from developing the condition;
(ii) delaying the onset of the condition (for example, osteoarthritis) in a subject, i.e. delaying a subject from developing the condition until later in the life of the subject;
(iii) limiting the occurrence of the condition (for example, osteoarthritis) in a subject, for example reducing the extent to which a subject is affected by the condition; or
(iv) preventing one or more symptoms of the condition (for example, osteoarthritis) in a subject, i.e. stopping the subject from developing one or more symptoms of the condition.

The terms "optionally", "preferably", "such as", "for example" and the like denote that the subsequently described feature, characteristic, event or circumstances may or may not occur, and that the description includes instances where said feature, characteristic, event or circumstances occurs and instances in which it does not occur. For the avoidance of doubt, it is to be understood that, in some embodiments of the invention, any feature, characteristic, event or circumstance described in the context of "optionally", "preferably", "such as", "for example" and the like may be disclaimed from the scope of the claims.

The term "subject" as used herein includes the meaning of any living human or animal (humans and horses are of particular interest) to which the treatment of the present invention is applied. Without limitation, exemplary subjects are defined further below in section D of the detailed description of the invention.

The term "elevated" as used herein includes the meaning that the substance (for example, a protein, such as TNF-$\alpha$ (alpha) or IL1-$\beta$ (beta)) is present in a higher amount in a subject with osteoarthritis when compared to the amount present in a subject without osteoarthritis.

The term "distal" as used here includes the meaning that administration of the Annexin A5 protein is not in the or each joint which has been diagnosed with osteoarthritis.

The term "therapeutically effective amount" refers to the amount of a drug, compound, protein (for example the Annexin A5 protein as defined herein) or pharmaceutical composition that is sufficient to effect beneficial or desired results including clinical results associated with the treatment or prophylaxis of osteoarthritis and/or a condition associated therewith. An effective amount can be administered in one or more administrations. For purposes of this invention, an effective amount of drug, compound, protein (for example the Annexin A5 protein as defined herein), pharmaceutical composition or veterinary composition is an amount sufficient to treat, ameliorate, reduce the intensity of and/or prevent osteoarthritis and/or a condition associated therewith. As is understood in the clinical context, an effective amount of a drug, compound, protein (for example the Annexin A5 protein as defined herein) or pharmaceutical composition may or may not be achieved when administered in conjunction (such as separately, sequentially or simultaneously) with another drug, compound, protein or pharmaceutical, such as those described elsewhere in this application. Thus, an "effective amount" may be considered in the context of administering one or more therapeutic agents, and a single agent may be considered to be given in an effective amount if, in conjunction with one or more other agents, a desirable result may be or is achieved.

DETAILED DESCRIPTION OF THE INVENTION

The present invention is based on the applicant's surprising realisation that Annexin A5 protein can be used in the prophylaxis and treatment of osteoarthritis, and one or more conditions associated therewith.

A. Osteoarthritis

The present invention is directed to the prophylaxis and treatment of osteoarthritis, and one or more conditions associated therewith.

Osteoarthritis is primarily a degenerative disease of the joint, which can cause pain through cartilage loss and morphological damage to other joint tissues.

Accordingly, in one embodiment, the osteoarthritis may be characterised by one or more of the following: damage to cartilage in the joint; loss of cartilage in the joint; degradation of collagen fibers in cartilage of the joint; disorganisation of collagen fibers in cartilage of the joint; decrease in proteoglycan content in cartilage of the joint; increase in water content of the joint; damage to synovium in the joint; loss of synovium in the joint; thickening of synovium in the joint; damage to ligament(s) in the joint; thickening of ligament(s) in the joint; damage to menisci in the joint; loss of menisci in the joint; increase in mineralisation in the joint; increase in calcification in the joint; death of chondrocytes (preferably, articular chondrocytes); death of cells; bone outgrowths (or osteophytes) in the joint; joint space narrowing; subchondral sclerosis (increased bone formation around the joint); subchondral cyst formation; swelling of the joint; and, inflammation of the joint.

Although the data in the Examples demonstrates that Annexin A5 protein can be used for the prophylaxis and treatment of osteoarthritis in general, those data demonstrate that Annexin A5 protein is particularly effective in the treatment and prophylaxis of osteoarthritis that is characterised by inflammation of the joint. The disease model used in the Examples the osteoarthritis phenotype is promoted by the addition of the pro-inflammatory cytokines IL1-β and TNF-α.

Preferably, the invention is directed to the prophylaxis and treatment of a form of osteoarthritis that is characterised by inflammation of the joint.

Preferably, the inflammation of the joint is one or more selected from: inflammation of tissue in the joint; inflammation of cartilage in the joint; and inflammation of synovium in the joint Preferably, the cartilage is articular cartilage.

In one preferred embodiment, the invention is directed to the prophylaxis and treatment of a form of osteoarthritis that is characterised by cell death, such as chondrocyte (preferably, articular chondrocyte) cell death.

In a further preferred embodiment, the invention is directed to the prophylaxis and treatment of a form of osteoarthritis that is characterised by inflammation of the joint and cell death, such as chondrocyte (preferably, articular chondrocyte) cell death.

Osteoarthritis can be divided into two general categories: primary osteoarthritis and secondary osteoarthritis. The main difference between those two categories is the underlying cause of the osteoarthritis. However, the resulting pathology of both primary osteoarthritis and secondary osteoarthritis can be similar. As discussed in the foregoing, in one embodiment the invention may be directed to the prophylaxis and treatment of osteoarthritis that is optionally primary osteoarthritis or secondary osteoarthritis. Preferably, the osteoarthritis is primary arthritis.

Primary osteoarthritis (sometimes also known as idiopathic osteoarthritis) is generally considered to be osteoarthritis without a specifically identified underlying cause. It is thought to occur due to aging and joint "wear and tear", sometimes with associated inflammation. Two sub-sets of primary osteoarthritis are generalised nodal osteoarthritis or erosive osteoarthritis. As discussed in the foregoing, in one embodiment the invention may be directed to the prophylaxis and treatment of primary osteoarthritis that is optionally selected from generalised nodal osteoarthritis or erosive osteoarthritis.

Generalised nodal osteoarthritis is the most common form of osteoarthritis. In some patients, generalised nodal osteoarthritis is thought to have a genetic component, due to family studies indicating that some subjects are genetically predisposed to developing such osteoarthritis.

Erosive osteoarthritis is also known as inflammatory osteoarthritis, and is generally considered to be a more aggressive form of osteoarthritis.

As mentioned in the foregoing, the Examples demonstrate that Annexin A5 protein is effective in the treatment and prophylaxis of osteoarthritis that is characterised by inflammation of the joint, such as erosive osteoarthritis.

Preferably, the invention is directed to the prophylaxis and treatment of primary erosive osteoarthritis.

Secondary osteoarthritis is osteoarthritis that can be more directly attributed to an underlying cause, such as a particular disease or a specific injury. As such, secondary osteoarthritis more often affects a subject at a younger age, when compared to primary osteoarthritis.

In one embodiment, the invention is directed to the prophylaxis and treatment of secondary osteoarthritis that may be caused by one or more of the following: a causative disease; an injury; and lifestyle.

Preferably, the causative disease is one or more selected from the list consisting of: alkaptonuria; diabetes; Ehlers-Danlos Syndrome; hemochromatosis; causative inflammatory disease; Marfan syndrome; and a joint infection.

Most preferably, the causative disease is an inflammatory disease.

Preferably, the causative inflammatory disease is one or more selected from the list consisting of: Perthes' disease; Lyme disease; and chronic arthritis which is not osteoarthritis (such as costochondritis, gout, rheumatoid arthritis, or psoriatic arthritis).

Preferably, the injury is one or more selected from the list consisting of: a joint injury; a broken bone; a ligament injury; and a congenital joint disorder.

Preferably, the lifestyle is one or more selected from the list consisting of: being overweight; being obese; and having a profession in which a joint (or joints) are put under a high strain (such as an athlete).

In non-human subjects (such as horses), osteoarthritis sometimes presents itself as lameness. In some embodiments, the invention is directed to the prophylaxis and treatment of osteoarthritis that is characterised by lameness.

More preferably, the osteoarthritis is acute symptomatic osteoarthritis.

By acute symptomatic osteoarthritis we include acute osteoarthritis and symptomatic osteoarthritis.

As described in the Examples, Annexin A5 is shown to reduce cell death and reduce inflammation. In accordance with the present invention, therefore, Annexin A5 protein may be used in treating osteoarthritis in which symptoms are caused by those two events, such as the treatment of acute symptomatic osteoarthritis.

For example, the invention may be directed to the prophylaxis and treatment of a form of acute symptomatic osteoarthritis that is characterised by inflammation of the joint.

The invention may be directed to the prophylaxis and treatment of a form of acute symptomatic osteoarthritis that is characterised by cell death, such as chondrocyte (preferably, articular chondrocyte) cell death.

The invention may be directed to the prophylaxis and treatment of a form of acute symptomatic osteoarthritis that is characterised by inflammation of the joint and cell death, such as chondrocyte (preferably, articular chondrocyte) cell death.

The invention may be directed to the prophylaxis and treatment of erosive acute symptomatic osteoarthritis.

Optionally, the osteoarthritis is traumatic osteoarthritis.

Each of the above categories and sub-categories of osteoarthritis would be known to one skilled in human medicine or veterinary medicine, as would be the causation of such osteoarthritis.

Osteoarthritis can be diagnosed based upon clinical examination (such as hard tissue enlargement and joint swelling), and a subject's history. Typically, clinical examination can use X-rays to confirm the diagnosis based upon the morphology of the joint affected.

Methods for the diagnosis of osteoarthritis are known to one skilled in medicine.

On diagnosis, osteoarthritis can be graded using internationally recognised systems, such as the WOMAC (Western Ontario and McMaster Universities Arthritis Index) (http://www.womac.org/womac/index.htm) scale and radiographic classification systems.

In one embodiment, the invention is directed to the prophylaxis and treatment of osteoarthritis that is characterised using a WOMAC scale and/or a radiographic classification system.

The WOMAC scale is used to grade osteoarthritis in a number of different types of joint, but most specifically used to grade osteoarthritis in the knee joint and hip joint. The scale takes into consideration pain (five aspects, each scored in a range of 0-20), stiffness (two aspects, each scored in a range of 0-8) and functional limitations (such as everyday activities like stair use, standing and bending—17 aspects, each scored in a range of 0-68).

The radiographic classification systems use X-rays to view the joint, and there are numerous sub-categories of classification—the Thompson grading (in particular, for lumbar disc degeneration, or intervertebral joint degradation), the Lane grading (in particular, for lumbar disc degeneration, or intervertebral joint degradation), the Kellgren grading (in particular, for cervical disc degeneration, intervertebral joint degradation, or cervical facet joint degeneration), the Pathria grading (in particular, for lumbar facet joint degeneration), the Weishaupt grading (in particular, for lumbar facet joint degeneration), Samilson-Prieto classification (in particular, for the glenohumeral joint), Kellgren-Lawrence grading (in particular, knee osteoarthritis), and the Tönnis classification (in particular, for hip degradation).

Preferably, the radiographic classification system is one or more selected from the list consisting of: Thompson grading; Lane grading; Kellgren grading; Pathria grading; Weishaupt grading; Samilson-Prieto classification; Kellgren-Lawrence grading; and, Tönnis classification.

Thompson grading is numbered from I to V (I being less extensive osteoarthritis and V being more extensive osteoarthritis), and takes into account the structure of the tissue, cartilage and the presence of osteophytes. Optionally, the invention is directed to the prophylaxis and treatment of osteoarthritis that satisfies the requirements of the Thompson grading radiographic classification system, and the subject exhibits a grading of I or more: for example, II; or II or more; or III; or III or more; or IV; or IV or V; or V.

Lane grading is numbered from 0-3 (0 being less extensive osteoarthritis and 3 being more extensive osteoarthritis), and takes into account joint space narrowing, the presence of osteophytes and the presence of sclerosis. Optionally, the invention is directed to the prophylaxis and treatment of osteoarthritis that satisfies the requirement of the Lane grading radiographic classification system, and the subject exhibits a grading of 0 or more: for example, 1; or 1 or more; or 2; or 2 or 3; or 3.

Kellgren grading is numbered from I-IV (I being less extensive osteoarthritis and IV being more extensive osteoarthritis), and takes into account joint space narrowing, the presence of osteophytes and the presence of sclerosis. Optionally, the invention is directed to the prophylaxis and treatment of osteoarthritis that satisfies the requirements of the Kellgren grading radiographic classification system, and the subject exhibits a grading of I or more: for example, II; or II or more; Ill; or III or IV; or IV.

Samilson-Prieto classification is graded "mild", "moderate", and "severe", and takes into account the size of the joint, the narrowing of the joint space and the presence of sclerosis. Optionally, the invention is directed to the prophylaxis and treatment of osteoarthritis that satisfies the requirement of the Samilson-Prieto radiographic classification system, and the subject exhibits a grading of mild or moderate or severe.

Kellgren-Lawrence grading is numbered from 0-4 (0 being less extensive osteoarthritis and 4 being more extensive osteoarthritis), and takes into account joint space narrowing, the presence of osteophytes and the presence of sclerosis. Optionally, the invention is directed to the prophylaxis and treatment of osteoarthritis that satisfies the requirement of the Kellgren-Lawrence grading radiographic classification system, and the subject exhibits a grading of 0 or more: for example, 1; or 1 or more; or 2; or 2 or more; or 3; or 3 or 4; or 4.

Tönnis classification is numbered from 0-3 (0 being no osteoarthritis, 1 being less extensive osteoarthritis and 3 being more extensive osteoarthritis), and takes into account joint space narrowing, the presence of bone cysts and the shape of the joint. Optionally, the invention is directed to the prophylaxis and treatment of osteoarthritis that satisfies the requirement of the radiographic classification system is Tönnis classification, and the subject exhibits a grading of 0 or more: for example, 1; or 1 or more; or 2; or 2 or 3; or 3. The way in which the forgoing classification and grading systems should be used and interpreted would be known to one skilled in medicine.

In one embodiment, the osteoarthritis may be characterised by elevated TNF-α (alpha) in the joint, or by elevated IL1-β (beta) in the joint, or elevated TNF-α and elevated IL1-β in the joint.

TNF-α is Tumor Necrosis Factor alpha, also known as TNF, cachexin, and cachectin. TNF-α is a cytokine which is often associated with inflammation. It is considered that TNF-α may be an inflammatory factor which can initiate osteoarthritis (Charlier et al., 2016, Int. J. Mol. Sci, 17, 2146), and in particular osteoarthritis in humans.

IL1-β is Interleukin-1 Family β, and it is a pro-inflammatory cytokine which binds the IL1 receptor. It is considered that IL1-β may be an inflammatory factor which can initiate osteoarthritis (Ross et al., 2012, Osteoarthritis and Cartilage, 20: 1583-1590), and in particular osteoarthritis in horses.

In one embodiment, the invention is directed to the prophylaxis and treatment of osteoarthritis that is characterised by elevated TNF-α (alpha).

In another embodiment, the invention is directed to the prophylaxis and treatment of osteoarthritis that is characterised by elevated IL1-β (beta).

In another embodiment, the invention is directed to the prophylaxis and treatment of osteoarthritis that is characterised by elevated TNF-α and elevated IL1-β.

Preferably, the osteoarthritis is traumatic osteoarthritis, and the traumatic osteoarthritis is characterised by elevated IL1-β.

In one embodiment, the invention may be directed to the prophylaxis and treatment of osteoarthritis that may be characterised by one or more of the following: elevated ICAM1 expression from cells in the joint; elevated RANKL expression from cells in the joint; elevated IL6 expression from cells in the joint; and elevated COX2 expression from cells in the joint.

ICAM1 is Intercellular Adhesion Molecule 1, and is also known as Cluster of Differentiation 54 (CD54). ICAM1 is a cell surface glycoprotein, which is often associated with osteoarthritis, as a marker of the disease.

RANKL is Receptor Activator of Nuclear factor Kappa-B Ligand, and is also known as tumor necrosis factor ligand superfamily member 11 (TNFSF11), TNF-related activation-induced cytokine (TRANCE), osteoprotegerin ligand (OPGL), and osteoclast differentiation factor (ODF). RANKL is a membrane protein and is a member of the TNF superfamily. RANKL is often associated with osteoarthritis, as a marker of the disease (Komori 2016, Int. J. Mol. Sci., 17).

IL6 is Interleukin 6, and it is a pro-inflammatory cytokine often associated with osteoarthritis (Mabey and Honsawek, 2015, World Journal of Orthopedics, 6(1):95-105).

COX2 is Cytochrome C Oxidase Subunit 2, and is also known by the abbreviations: COXII, COII, and MT-CO2. COX2 is a component of the Cytochrome C Oxidase enzyme, and is associated with osteoarthritis as a biomarker of joint inflammation.

By expression we include the presence of RNA (ribonucleic acid) and/or protein, corresponding to the gene. It would be known to one skilled in molecular biology how to detect RNA expression and protein expression.

In one embodiment, the invention is directed to the prophylaxis and treatment of osteoarthritis that is characterised by elevated ICAM1 expression from cells in the joint.

In another embodiment, the invention is directed to the prophylaxis and treatment of osteoarthritis that is characterised by elevated RANKL expression from cells in the joint.

In another embodiment, the invention is directed to the prophylaxis and treatment of osteoarthritis that is characterised by elevated IL6 expression from cells in the joint.

In another embodiment, the invention is directed to the prophylaxis and treatment of osteoarthritis that is characterised by elevated COX2 expression from cells in the joint.

Preferably, the ICAM1 expression is ICAM1 protein expression on the surface of the cell.

Preferably, the RANKL expression is RANKL protein expression on the surface of the cell.

Preferably, the cell or cells are one or more cell type selected from the list consisting of: chondrocytes (most preferably, articular chondrocytes); chondroblasts; and osteoblasts.

It would be understood by one skilled in molecular biology how the forgoing proteins and expression could be measured.

In one embodiment, the invention may be directed to the prophylaxis and treatment of osteoarthritis that may be characterised by one or more of the following: reduced damage to cartilage in the joint; inhibited damage to cartilage in the joint; reduced loss of cartilage in the joint; reduced degradation of collagen fibers in cartilage of the joint; reduced disorganisation of collagen fibers in cartilage of the joint; increase in proteoglycan content in cartilage of the joint; decrease in water content of the joint; reduced damage to synovium in the joint; reduced loss of synovium in the joint; inhibited damage to cartilage in the joint; reduced damage to cartilage in the joint; reduction in the size of synovium in the joint; reduced damage to ligament(s) in the joint; inhibited damage to cartilage in the joint; reduction in the size of ligament(s) in the joint; reduced damage to menisci in the joint; inhibited damage to cartilage in the joint; reduced loss of menisci in the joint; reduced mineralisation in the joint; inhibited mineralisation in the joint; reduced calcification in the joint; inhibited mineralisation in the joint; inhibition of chondrocyte (preferably, articular chondrocyte) death; reduction of chondrocyte (preferably, articular chondrocyte) cell death; inhibition of cell death; reduction of bone outgrowths (or osteophytes) in the joint; inhibition of bone outgrowths; joint space increasing; reduction subchondral sclerosis (increased bone formation around the joint); inhibited subchondral sclerosis; reduced subchondral cyst formation; inhibited subchondral cyst formation; reduced swelling of the joint; inhibited inflammation of the joint; and, reduced inflammation of the joint.

Preferably, the prophylaxis and treatment of osteoarthritis may be characterised by inhibition of chondrocyte (preferably, articular chondrocyte) cell death.

Preferably, the prophylaxis and treatment of osteoarthritis may be characterised by reduction of chondrocyte (preferably, articular chondrocyte) cell death.

Preferably, the prophylaxis and treatment of osteoarthritis may be characterised by inhibited inflammation of the joint.

Preferably, the prophylaxis and treatment of osteoarthritis may be characterised by reduced inflammation of the joint.

B. Joints

The present invention is directed to the prophylaxis and treatment of osteoarthritis in one or more joints of a subject. As is known to one skilled in medicine, a joint is a connection between bones of the body.

Joints in which the present invention can be employed for the prophylaxis and treatment of osteoarthritis can be categorised in a number of ways, for example by functional classification, structural classification, biomedical classification, or anatomical classification. These classifications would be known to one skilled in medicine.

The functional classification of joints relates to the type and degree of movement that the joints allow, and is divided into three different categories: synarthrosis (which are joints that permit little or no mobility—generally fibrous joints); amphiarthrosis (which are joints that permit slight movement—generally cartilaginous joints); and, synovial joints—also known as diarthrosis joints (which move freely).

As discussed in the foregoing, in one embodiment the or each joint in which the present invention can be employed for the prophylaxis and treatment of osteoarthritis may be selected from the list consisting of: a synovial joint; an amphiarthrosis joint; and a synarthrosis joint.

The classification of synovial joints in which the present invention can be employed for the prophylaxis and treatment of osteoarthritis can be further divided into the following six groups: a plane joint (also known as an arthrodial joint, a gliding joint, or a plane articulation, and which allows for a gliding movement); a ball and socket joint (also known as a spheroidal joint, and which allows for movement around a number of axes); a hinge joint (also known as a ginglymus joint, and which allows for movement in just one plane); a pivot joint (also known as a trochoid joint, a rotary joint, or a lateral ginglymus, and which also allows for movement in just one plane); a condyloid joint (also known as a condylar joint, an ellipsoidal joint, or a bicondylar joint, and which allows for movement in two planes); and a saddle joint (also known as a sellar joint, or an articulation by reciprocal reception, and which also allows for movement in two planes). All of these six groups of synovial joint would be known to one skilled in medicine.

Preferably, the synovial joint in which the present invention can be employed for the prophylaxis and treatment of osteoarthritis is one or more synovial joint selected from the list consisting of: a plane joint; a ball and socket joint; a hinge joint; a pivot joint; a condyloid joint; and a saddle joint.

Preferably, the plane joint in which the present invention can be employed for the prophylaxis and treatment of osteoarthritis is one or more plane joint selected from the list consisting of: a costovertebral joint; a facet joint; a midcarpal joint; a carpometacarpal finger joint; an intermetacarpal joint; a sacroiliac joint; a zygapophyseal joint; a sternocostal joint; a subtalar joint (or talocalcaneal joint); and, an acromioclavicular joint.

Preferably, the ball and socket joint in which the present invention can be employed for the prophylaxis and treatment of osteoarthritis is one or more ball and socket joint selected from the list consisting of: a tibiotarsal joint; a tibiofibular joint; a shoulder joint (also known as the scapulohumeral joint); a glenohumeral joint; a talocalcaneonavicular joint; and, a hip joint (also known as the coxofemoral joint).

Preferably, the hinge joint in which the present invention can be employed for the prophylaxis and treatment of osteoarthritis is one or more hinge joint selected from the list consisting of: an ankle joint; an elbow joint (also known as the humeroradial joint); a temporomandibular joint; an interphalangeal joint; a stifle joint; and, a knee joint.

Preferably, the pivot joint in which the present invention can be employed for the prophylaxis and treatment of osteoarthritis is one or more pivot joint selected from the list consisting of: an atlantoaxial joint; an atlanto-axial joint; a proximal radioulnar joint; a hock joint; a tarsal joint; a talocalcaneonavicular joint; a calcaneocuboid joint; and, a distal radioulnar joint.

Preferably, the condyloid joint in which the present invention can be employed for the prophylaxis and treatment of osteoarthritis is one or more condyloid joint selected from the list consisting of: an atlanto-occipital joint; a radiocarpal joint; a metatarsophalangeal joint; a wrist joint; an intercarpal joint; a radiocarpal joint; and, a metacarpophalangeal joint (also known as the fetlock joint).

Preferably, the saddle joint in which the present invention can be employed for the prophylaxis and treatment of osteoarthritis is one or more saddle joint selected from the list consisting of: a carpometacarpal thumb joint; a calcaneocuboid joint; and, a sternoclavicular joint.

More preferably, in one embodiment, the joint in which the present invention can be employed for the prophylaxis and treatment of osteoarthritis is a metacarpophalangeal joint.

More preferably, in another embodiment, the joint in which the present invention can be employed for the prophylaxis and treatment of osteoarthritis is a carpal joint.

More preferably, in another embodiment, the joint in which the present invention can be employed for the prophylaxis and treatment of osteoarthritis is a tibiotarsal joint.

More preferably, in another embodiment, the joint in which the present invention can be employed for the prophylaxis and treatment of osteoarthritis is an intercarpal joint.

More preferably, in another embodiment, the joint in which the present invention can be employed for the prophylaxis and treatment of osteoarthritis is a radiocarpal joint.

More preferably, in another embodiment, the joint in which the present invention can be employed for the prophylaxis and treatment of osteoarthritis is a shoulder joint.

More preferably, in another embodiment, the joint in which the present invention can be employed for the prophylaxis and treatment of osteoarthritis is a knee joint.

More preferably, in another embodiment, the joint in which the present invention can be employed for the prophylaxis and treatment of osteoarthritis is an elbow joint.

Preferably, in another embodiment, the amphiarthrosis joint in which the present invention can be employed for the prophylaxis and treatment of osteoarthritis is a symphysis (for example, a joint between vertebral discs, i.e. an intervertebral joint).

Preferably, in another embodiment, the fibrous joint in which the present invention can be employed for the prophylaxis and treatment of osteoarthritis is one or more fibrous joint selected from the list consisting of: a suture, a distal tibiofibular joint; a gomphosis; a plane suture; a limbous suture; a schindylesis; a denticulate suture; and a serrate suture.

As would be known to one skilled in medicine, the aforementioned joints discussed in relation to the functional classification of joints can also be categorised based upon the structural classification, biomedical classification, or anatomical classification.

The structural classification of joints relates to the type of binding tissue which connects the bones of the joint, and is divided into three different categories: fibrous joints (which are joined by connective tissue with high amounts of collagen fibers); cartilaginous joints (which are joined by cartilage); and synovial joints (which have a synovial cavity and are joined by connective tissue and ligaments).

In one embodiment, the joint in which the present invention can be employed for the prophylaxis and treatment of osteoarthritis is one or more selected from the list consisting of: a fibrous joint; a cartilaginous joint; and, a synovial joint.

The biomedical classification of joints relates to the anatomy of the joint and the biomechanical properties of the joint, and is divided into three different categories: simple joints (which have two articulation surfaces—for example, the shoulder joint or hip joint); compound joints (which have three of more articulation surfaces—for example, the radiocarpal joint); and, complex joints (which have two or more articulation surfaces and an articular disc or meniscus—for example, the knee joint).

In one embodiment, the joint in which the present invention can be employed for the prophylaxis and treatment of osteoarthritis is one or more selected from the list consisting of: a simple joint; a compound joint; and, a complex joint.

The anatomical classification of joints is divided into 11 different categories, which are: joints of the hand; elbow joints; wrist joints; axillary articulations; sternoclavicular joints; vertebral articulations; temporomandibular joints; sacroiliac joints; hip joints; knee joints; and, articulations of the foot.

In one embodiment, the joint in which the present invention can be employed for the prophylaxis and treatment of osteoarthritis is one or more selected from the list consisting of: joints of the hand; elbow joints; wrist joints; axillary articulations; sternoclavicular joints; vertebral articulations; temporomandibular joints; sacroiliac joints; hip joints; knee joints; and, articulations of the foot.

It would be known to one skilled in veterinary medicine or human medicine that joint structure, classification and naming differs between human subjects and non-human subjects (such as horses and the other non-human subjects discussed in section D). Therefore, non-human equivalents of human joints are included. For example, the wrist joint in humans is equivalent to the knee joint in some non-humans (such as horses), the knee joint in humans is equivalent to the stifle joint in some non-humans (such as horses), and the tarsal joint in humans is equivalent to the hock joint in some non-humans (such as horses).

In a horse, the wrist joint is formed from the antebrachiocarpal joint, middle carpal joint, and carpometacarpal joint. Optionally, when the subject is a non-human subject (such as a horse) the joint in which the present invention can be employed for the prophylaxis and treatment of osteoarthritis is one or more selected from the list consisting of: antebrachiocarpal joint; middle carpal joint; and, carpometacarpal joint.

In a horse, the stifle joint is formed from the femoropatellar joint, medial femorotibial joint, and lateral femorotibial joint. Optionally, when the subject is a non-human subject (such as a horse) the joint in which the present invention can be employed for the prophylaxis and treatment of osteoarthritis is one or more selected from the list consisting of: a femoropatellar joint; a medial femorotibial joint; and, lateral femorotibial joint.

In a horse, the hock joint is formed from the arsocrural joint, the proximal intertarsal joint, the distal intertarsal joint, the tarsometatarsal joint and the talocalcaneal joint. Optionally, when the subject is a non-human subject (such as a horse) the joint in which the present invention can be employed for the prophylaxis and treatment of osteoarthritis is one or more selected from the list consisting of: an arsocrural joint; a proximal intertarsal joint; a distal intertarsal joint; a tarsometatarsal joint; and a talocalcaneal joint.

In one embodiment, the osteoarthritis may be in one or more joints: for example, 2 or more joints; or 3 or more joints; or 4 or more joints; or 5 or more joints; or 6 or more joints; or 7 or more joints; or 8 or more joints; or 9 or more joints; or 10 or more joints; or 11 or more joints; or 12 or more joints; or 13 or more joints; or 14 or more joints; or 15 or more joints; or 16 or more joints; or 17 or more joints; or 18 or more joints; or 19 or more joints; or 20 or more joints; or 21 or more joints; or 22 or more joints; or 23 or more joints; or 24 or more joints; or 25 or more joints; or 26 or more joints; or 27 or more joints; or 28 or more joints; or 29 or more joints; or 30 or more joints; or 31 or more joints; or 32 or more joints; or 33 or more joints; or 34 or more joints; or 35 or more joints; or 36 or more joints; or 37 or more joints; or 38 or more joints; or 39 or more joints; or 40 or more joints.

C. Annexin A5

The Annexin A5 protein for use in all aspects of the present invention may comprise, consist essentially of, or consist of, a protein consisting of the sequence of Annexin A5, such as the sequence of human Annexin A5. Preferably the human Annexin A5 protein is a protein consisting of the sequence of SEQ ID NO:1, as shown below, either with or without the N-terminal methionine. Preferably the Annexin A5 protein is a recombinant human Annexin A5 protein, for example, a protein created by recombinant expressing a gene encoding a protein having the sequence of SEQ ID NO: 1 in a recombinant host cell organism, such as a recombinant *E. coli* host.

The sequence of the protein encoded by the human Annexin A5 gene is defined by SEQ ID NO: 1 as follows—

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
                100                 105                 110

Ile Ile Ala Ser Arg Thr Pro Glu Glu Leu Arg Ala Ile Lys Gln Val
            115                 120                 125

Tyr Glu Glu Glu Tyr Gly Ser Ser Leu Glu Asp Asp Val Val Gly Asp
        130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
                180                 185                 190
```

-continued

```
Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320
```

In another embodiment, the Annexin A5 protein may comprise, consist essentially of, or consist of, a variant or mutant of a protein consisting of the sequence of Annexin A5, such as the sequence of human Annexin A5 (optionally, a protein consisting of the sequence of SEQ ID NO:1, either with or without the N-terminal methionine). For example, the sequence of the variant or mutant may differ from the sequence of SEQ ID NO: 1 (either with, or without, the N-terminal methionine) at any one or more positions, such as at, or up to, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160 or more positions.

In another embodiment, the Annexin A5 protein may comprise, consist essentially of, or consist of, a biologically active fragment of mature Annexin A5, such as human Annexin A5 (optionally, a protein consisting of the sequence of SEQ ID NO:1, either with or without the N-terminal methionine) or of a variant or mutant thereof.

Biologically active fragments of Annexin A5 share a functional or binding property with full length Annexin A5. Epitopic fragments of Annexin A5 bind to a monoclonal antibody that binds to full length Annexin A5. "Activity" of Annexin A5 shall mean any binding function performed by that protein, further examples of which are defined further below.

A biologically active fragment of the Annexin A5 protein, which can be used in the present invention, may comprise at least about 50 contiguous amino acids, usually at least about 100 contiguous amino acids, at least about 150 contiguous amino acids, at least about 200 contiguous amino acids, at least about 250 contiguous amino acids, at least about 260 contiguous amino acids, at least about 270 contiguous amino acids, at least about 280 contiguous amino acids, at least about 290 contiguous amino acids, at least about 300 contiguous amino acids, at least about 310 contiguous amino acids, and which may include up to about 320 contiguous amino acids of an Annexin A5 protein, including without limitation human Annexin A5 protein (optionally, a protein consisting of the sequence of SEQ ID NO:1, either with or without the N-terminal methionine), or modifications thereof, and may further include fusion polypeptides as known in the art in addition to the provided sequences. The Annexin A5 sequence may be from any mammalian or avian species, e.g. primate sp., particularly humans; rodents, including mice, rats and hamsters; rabbits; equines, bovines, canines, felines; etc. Of particular interest is the human Annexin A5 protein (optionally, a protein consisting of the sequence of SEQ ID NO:1, either with or without the N-terminal methionine).

Typically, the Annexin A5 protein is monomeric Annexin A5, although it may alternatively include dimers, fusions proteins, PEGylated versions, and other modifications. In an alternative embodiment, the Annexin A5 protein is not a dimer, a fusion protein, or a PEGylated version; or the composition and/or formulation does not comprise an Annexin A5 protein that is a dimer, a fusion protein, or a PEGylated version. By an Annexin A5 protein that is a dimer, we particularly include a dimer of two monomeric Annexin A5 proteins which are attached via covalent bonds.

The Annexin A5 protein may include one or more of the following:

a) a protein comprising, consisting essentially of, or consisting of the sequence of human Annexin A5 (optionally, a protein consisting of the sequence of SEQ ID NO:1, either with or without the N-terminal methionine);
b) a mammalian orthologue of human Annexin A5;
c) an allelic or genetic variant of a) or b);
d) a functional analogue or variant of Annexin which is a protein which is more than 50%, 60%, 70%, 75%, such as more than 80%, 85%, more than 90%, or even more preferably more than 95% or 99% identical to human Annexin A5, SEQ ID NO:1 either with, or without, the N-terminal methionine;
e) a biologically active fragment of any of a), b), c), or d);
f) a monomer consisting of, dimer comprising or consisting of, or a fusion protein comprising, any of a), b), c), d) or e); and
g) a PEGylated variant of any of a), b), c), d), e) or f).

In a further embodiment, the Annexin A5 protein may, or may not be, be a fusion protein, which fusion protein comprises, consists essentially of, or consists of: (a) one or more protein sequences comprising the sequence of fusion partner that is/are fused to; (b) one or more protein sequences that comprises, consists essentially of, or consists of, a protein having the sequence of an Annexin A5 protein as defined above, (for example, human Annexin A5 (such as SEQ ID NO:1, either with or without the N-terminal methionine), or a variant, analogue, mutant or biologically active fragment thereof, or dimer as described above. For example, without limitation, the fusion protein may have a general structure selected from:

in the case of the fusion of two amino acid sequences, for example: H2N-(a)-(b)-COOH; or H2N-(b)-(a)-COOH; or in the case of the fusion of three amino acid sequences, for example: H2N-(a)-(b)-(a)-COOH; or H2N-(b)-(a)-(b)-COOH; or H2N-(a)-(b)-(b)-COOH; or H2N-(b)-(b)-(a)-COOH; or H2N-(a)-(a)-(b)-COOH; or H2N-(b)-(a)-(a)-COOH; or in the case of the fusion of four amino acid sequences, for example: H2N-(a)-(a)-(a)-(b)-COOH; or H2N-(a)-(a)-(b)-(a)-COOH; or H2N-(a)-(b)-(a)-(a)-COOH; or H2N-(b)-(a)-(a)-(a)-COOH; or H2N-(a)-(a)-(b)-(b)-COOH; or H2N-(a)-(b)-(a)-(b)-COOH; or H2N-(b)-(a)-(a)-(b)-COOH; or H2N-(a)-(b)-(b)-(a)-COOH; or H2N-(b)-(a)-(b)-(a)-COOH; or H2N-(b)-(b)-(a)-(a)-COOH; or H2N-(a)-(b)-(b)-(b)-COOH; or H2N-(b)-(a)-(b)-(b)-COOH; or H2N-(b)-(b)-(a)-(b)-COOH; or H2N-(b)-(b)-(b)-(a)-COOH; or H2N-(a)-(b)-(b)-(b)-COOH; or in the case of the fusion of five amino acid sequences, for example: or H2N-(a)-(a)-(a)-(a)-(b)-COOH; or H2N-(a)-(a)-(a)-(b)-(a)-COOH; or H2N-(a)-(a)-(b)-(a)-(a)-COOH; or H2N-(a)-(b)-(a)-(a)-(a)-COOH; or H2N-(b)-(a)-(a)-(a)-(a)-COOH; or H2N-(a)-(a)-(a)-(b)-(b)-COOH; or H2N-(a)-(a)-(b)-(a)-(b)-COOH; or H2N-(a)-(b)-(a)-(a)-(b)-COOH; or H2N-(b)-(a)-(a)-(a)-(b)-COOH; or H2N-(a)-(a)-(b)-(b)-(a)-COOH; or H2N-(a)-(b)-(a)-(b)-(a)-COOH; or H2N-(b)-(a)-(a)-(b)-(a)-COOH; or H2N-(a)-(b)-(b)-(a)-(a)-COOH; or H2N-(b)-(a)-(b)-(a)-(a)-COOH; or H2N-(b)-(b)-(a)-(a)-(a)-COOH; or H2N-(a)-(a)-(b)-(b)-(b)-COOH; or H2N-(a)-(b)-(a)-(b)-(b)-COOH; or H2N-(b)-(a)-(a)-(b)-(b)-COOH; or H2N-(a)-(b)-(b)-(a)-(b)-COOH; or H2N-(b)-(a)-(b)-(a)-(b)-COOH; or H2N-(b)-(b)-(a)-(a)-(b)-COOH; or H2N-(a)-(b)-(b)-(b)-(a)-COOH; or H2N-(b)-(a)-(b)-(b)-(a)-COOH; or H2N-(b)-(b)-(a)-(b)-(a)-COOH; or H2N-(b)-(b)-(b)-(a)-(a)-COOH; or H2N-(a)-(b)-(b)-(b)-(b)-COOH; or H2N-(b)-(a)-(b)-(b)-(b)-COOH; or H2N-(b)-(b)-(a)-(b)-(b)-COOH; or H2N-(b)-(b)-(b)-(a)-(b)-COOH; or H2N-(b)-(b)-(b)-(b)-(a)-COOH, wherein (a) and (b) are as defined above in this paragraph. In the case of multiple fusion partner proteins, as defined by (a), the multiple fusion partners may be same or different. Any fusion partner of interest may be used. For example, the fusion partner polypeptide sequence(s) may be suitable to extend the half-life of the molecule within a patient's circulatory system and/or add further functionality to the molecule, such as to add additional therapeutic properties (e.g. anti-coagulant, cell inhibition and/or killing, etc.). In the case of fusion proteins comprising multiple protein sequences having the sequence of human Annexin A5 (such as SEQ ID NO:1), either with or without the N-terminal methionine, or a variant or mutant thereof, or dimer as described above, as defined by (b), those proteins may be the same or different.

In one aspect of the present invention, the Annexin A5 used in accordance with the present invention consists human Annexin A5, and/or or PEGylated or dimeric forms thereof. That is, in one embodiment, the Annexin A5 is not bound to, conjugated to, or otherwise attached and/or formulated with any other moieties, including active agents. It is particularly preferred that the Annexin A5 protein is not bound to, conjugated to or otherwise attached and/or formulated with a radioactive moiety, such as a radionucleotide, for example Tin-117m. The therapeutic and prophylactic activity of the Annexin A5 protein, and formulations and/or compositions thereof, in accordance with the present invention preferably rely primarily or exclusively on the biological activity of the Annexin A5 moiety. Accordingly, the definition of the Annexin A5 protein in accordance with the present invention most preferably may exclude the Tin-117m annexin V molecules of WO 2014/197681.

In accordance with one aspect of the present invention, the Annexin A5 may be used as the sole active agent in the therapies described above.

In particular embodiments, the functional analogue, mutant or variant of Annexin A5 according to the invention is more than 50%, 60%, 70%, 75%, such as more than 80%, 85%, more than 90%, or even more preferably more than 95% or 99% identical to human Annexin A5, SEQ ID NO:1 either with, or without, the N-terminal methionine.

The percent identity between two amino acid sequences is determined as follows. First, an amino acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence followed by multiplying the resulting value by 100. For example, if a sequence is compared to the sequence set forth in SEQ ID NO:1 (the length of the sequence set forth in SEQ ID NO:1 is 320) and the number of matches is 288, then the sequence has a percent identity of 90 (i.e., 288÷320*100=90) to the sequence set forth in SEQ ID NO:1.

Thus, a functional analogue, mutant or variant of Annexin A5 may be a protein wherein at one or more positions there have been amino acid insertions, deletions, or substitutions, either conservative or non-conservative, provided that such changes result in a protein whose basic properties to function in an equivalent manner to Annexin A5 have not significantly been changed. "Significantly" in this context means that one skilled in the art would say that the properties of the variant may still be different but would not be unobvious over the ones of the original protein.

By "conservative substitutions" is intended combinations such as Gly, Ala; Val, Ile, Leu; Asp, Glu; Asn, Gln; Ser, Thr; Lys, Arg; and Phe, Tyr.

Such variants and mutants may be made using the methods of protein engineering and site-directed mutagenesis which are well known in the art.

The functional analogue, mutant or variant of Annexin A5 according to the invention may be a dimer of Annexin A5 (such as DiAnnexin) or a functional analogue or variant thereof, or may be a PEGylated Annexin A5 or a functional analogue or variant thereof. DiAnnexinA5 and PEGylated AnnexinA5 are disclosed in WO 02/067857.

PEGylation is a method well known to those skilled in the art wherein a polypeptide or peptidomimetic compound (for the purposes of the present invention, Annexin A5 or the functional analogue or variant) is modified such that one or more polyethylene glycol (PEG) molecules are covalently attached to the side chain of one or more amino acids or derivatives thereof. It is one of the most important molecule altering structural chemistry techniques (MASC). Other MASC techniques may be used; such techniques may improve the pharmacodynamic properties of the molecule, for example extending its half-life in vivo. A PEG-protein conjugate is formed by first activating the PEG moiety so that it will react with, and couple to, the protein or peptidomimetic compound of the invention. PEG moieties vary considerably in molecular weight and conformation, with the early moieties (monofunctional PEGs; mPEGs) being linear with molecular weights of 12 kDa or less, and later moieties being of increased molecular weights. PEG2, a recent innovation in PEG technology, involves the coupling of a 30 kDa (or less) mPEG to a lysine amino acid (although PEGylation can be extended to the addition of PEG to other amino acids) that is further reacted to form a branched structure that behaves like a linear mPEG of much greater molecular weight (Kozlowski et al., 2001). Methods that may be used to covalently attach the PEG molecules to polypeptides are further described in Roberts et al. (2002) Adv Drug Deliv Rev, 54, 459-476; Bhadra et al. (2002) Pharmazie 57, 5-29; Kozlowski et al. (2001) J Control Release 72, 217-224; and Veronese (2001) Biomaterials 22, 405-417 and references referred to therein.

The advantages of PEGylation include reduced renal clearance which, for some products, results in a more sustained adsorption after administration as well as restricted distribution, possibly leading to a more constant and sustained plasma concentrations and hence an increase in clinical effectiveness (Harris et al. (2001) Clin Pharmacokinet 40, 539-551). Further advantages can include reduced immunogenicity of the therapeutic compound (Reddy (2001) Ann Pharmacother, 34, 915-923), and lower toxicity (Kozlowski et al. (2001), Biodrugs 15, 419-429).

The functional analogue, mutant or variant of Annexin A5 can be a fusion protein comprising the sequence of Annexin A5 or a variant or biologically active fragment thereof. Thus, for example, Annexin A5 or a variant or biologically active thereof can be fused to one or more fusion partner polypeptide sequence(s) so as to extend the half-life of the molecule within a patient's circulatory system and/or add further functionality to the molecule. In one embodiment, fusion proteins of Annexin A5 are excluded from the present invention.

A "functional" analogue, mutant, variant or biologically active fragment of Annexin A5 may be capable of binding to phosphatidylserine on a biological membrane, preferably to a level that is at least 10%, 20%, 30%, 40%, 50%, 60%, 70%, 80%, 90%, 95%, 99% or about 100% of that displayed by human Annexin A5 (SEQ ID NO:1) under the same conditions. A suitable method for measuring Annexin A5 binding to phosphatidylserine on a biological membrane is known in the art (Vermes et al. (1995) J Immunol Methods, 184(1): p. 39-51).

A "functional" analogue, mutant, variant or biologically active fragment of Annexin A5 may, additionally, or alternatively, possess at least 10%, 20%, 30%, 40%, 50%, 60%, 70%, 80%, 90%, 95%, 99% or about 100% of the therapeutic activity human Annexin A5 (such as SEQ ID NO:1) when used at the same (i.e. molar equivalent) dosage, for treatment in accordance with the present invention. In this context, the therapeutic activity of a "functional" analogue, mutant, variant or biologically active fragment of Annexin A5 may be determined, compared to that of human Annexin A5 (such as SEQ ID NO:1), by comparing the ability of a molar equivalent amount of the functional analogue or variant and of human Annexin A5.

A functional analogue, mutant, variant or biologically active fragment of Annexin A5 may, optionally, consist of the sequence of human Annexin A5 (such as SEQ ID NO:1), either with, or without, the N-terminal methionine, with no greater than 50, 40, 30, 20, 10, 5, 4, 3, 2 or 1 consecutive or non-consecutive additional amino acid; and/or no greater than 50, 40, 30, 20, 10, 5, 4, 3, 2 or 1 consecutive or non-consecutive amino acid deletions; and/or no greater than 50, 40, 30, 20, 10, 5, 4, 3, 2 or 1 consecutive or non-consecutive amino acid substitutions.

D. Subjects for Treatment

The subject to be treated in accordance with the present invention may be a human subject or a non-human subject.

In one embodiment, the subject is a human subject.

In another embodiment, the subject is a non-human subject, and may be selected from the group consisting of: a mammalian subject, which is not a human; a bird; an amphibian; and a reptile.

Preferably, the mammalian subject, which is not a human, is one or more selected from the list consisting of: an equine; a bovine; a camel; a pig; a llama; an alpaca; a sheep; a goat; a canine; a feline; a rabbit; or a rodent.

Preferably, the equine is a horse or donkey.

More preferably, the subject is a horse, optionally a thoroughbred horse and/or a racehorse.

Most preferably, the subject is a horse or human.

In some embodiments, the present invention can be employed for the prophylaxis and treatment of osteoarthritis that may be characterised by lameness, and the subject may be a non-human subject.

In one preferred embodiment, the osteoarthritis is characterised by lameness, and the subject is a horse.

As mentioned in the foregoing, although not exclusively, osteoarthritis is generally thought to be a disease caused, in part, by "wear and tear", which is often caused by a subject's lifestyle. Due to the nature in which thoroughbred horses and racehorses are trained, it is generally considered that such horse subjects are of high risk of developing osteoarthritis. Therefore, Annexin A5 protein may be particularly effective at treating osteoarthritis in such horse subjects.

Preferably, the bovine is one or more selected from the list consisting of: a cow; a buffalo; a bison; and a yak.

Preferably, the rodent is one or more selected from the list consisting of: a mouse; a rat; a chinchilla; a guinea pig; and a squirrel.

Preferably, the bird is one or selected from the list consisting of: an ostrich; a chicken; a goose; a duck; a turkey; a quail; and a pigeon.

Preferably, the reptile is one or more selected from the list consisting of: a snake; a lizard; a crocodile; an alligator; a tortoise; and a turtle.

Preferably, the amphibian is a frog or a salamander.

In one embodiment, the subject may not be a juvenile and/or may have completed physical growth.

It would be known whether a subject has completed physical growth, to one skilled in human medicine or veterinary medicine. By the term "completed physical growth", it is included that the subject is physically mature and/or the subject is considered an adult subject.

In one embodiment, the subject may been sexually mature.

It would be known whether a subject is sexually mature, to one skilled in human medicine or veterinary medicine. By the term "sexually mature", it is included that the subject is capable of conceiving offspring and/or the subject has completed puberty.

In one embodiment, the subject may be an elderly subject. The exact age at which a subject is considered elderly can vary, in particular dependent on the species. Optionally, the term elderly indicates that the age of the subject is greater than 50%, 60%, 70%, 80%, 90% or 100% of the mean average life-expectancy of the species to which the subject belong (either judged world-wide, or within the particularly country in which the subject resides).

It would be known to one skilled in human medicine or veterinary medicine whether a subject is elderly.

In one embodiment, the subject may be a human subject and is 45 or more years of age: for example, 46 or more years of age; 47 or more years of age; 48 or more years of age; 49 or more years of age; 50 or more years of age; 51 or more years of age; 52 or more years of age; 53 or more years of age; 54 or more years of age; 55 or more years of age; 56 or more years of age; 57 or more years of age; 58 or more years of age; 59 or more years of age; 60 or more years of age; 61 or more years of age; 62 or more years of age; 63 or more years of age; 64 or more years of age; 65 or more years of age; 66 or more years of age; 67 or more years of age; 68 or more years of age; 69 or more years of age; 70 or more years of age; 75 or more years of age; 80 or more years of age; 85 or more years of age; 90 or more years of age; 95 or more years of age; or 100 or more years of age.

In one preferred embodiment, the subject may be a human subject and is 55 or more years of age.

In another preferred embodiment, the subject may be a human subject and is 65 or more years of age.

In another preferred embodiment, the subject may be a human subject and is 75 or more years of age.

In one embodiment, the subject may be a horse subject and is 5 or more years of age: for example, 6 or more years of age; 7 or more years of age; 8 or more years of age; 9 or more years of age; 10 or more years of age; 11 or more years of age; 12 or more years of age; 13 or more years of age; 14 or more years of age; 15 or more years of age; 16 or more years of age; 17 or more years of age; 18 or more years of age; 19 or more years of age; 20 or more years of age; 21 or more years of age; 22 or more years of age; 23 or more years of age; 24 or more years of age; 25 or more years of age; 26 or more years of age; 27 or more years of age; 28 or more years of age; 29 or more years of age; 30 or more years of age; 31 or more years of age; 32 or more years of age; 33 or more years of age; 34 or more years of age; 35 or more years of age; 36 or more years of age; 37 or more years of age; 38 or more years of age; 39 or more years of age; or 40 or more years of age.

In one preferred embodiment, the subject may be a horse subject and is 15 or more years of age.

In another preferred embodiment, the subject may be a horse subject and is 25 or more years of age.

As mentioned in the forgoing, although not exclusively, osteoarthritis is generally thought to be a disease that affects the elderly. Therefore, Annexin A5 protein might be particularly effective in the treatment or prophylaxis of osteoarthritis in elderly subjects.

E. Administrative Regimes

Dosages & Timings:

In accordance with the various embodiments of the present invention the Annexin A5 protein, or a pharmaceutically, or veterinarially, acceptable composition comprising the Annexin A5 protein may be administered at a therapeutically effective dosage to treat the subject in a manner as defined above.

In one embodiment, in accordance with any of the foregoing aspects of the present invention, the Annexin A5 protein may be administered to the or each joint. Preferably, the administration to the joint is into one or more of the following: articular capsule; cartilage (in particular, articular cartilage); joint cavity; and, synovial fluid.

In one preferred embodiment, the administration to the joint comprises administration of the Annexin A5 protein directly into the joint cavity in the or each joint to be treated.

In another preferred embodiment, the administration to the joint comprises administration of the Annexin A5 protein directly into the synovial fluid of the or each joint to be treated.

In another preferred embodiment, the Annexin A5 may be administered distal from the or each joint to be treated. For example, the Annexin A5 may be administered distal from the or each joint into the subject's blood. In accordance with one preferred option, the Annexin A5 is administered systemically. Most preferably, the Annexin A5 is administered systemically by injection.

In another preferred embodiment, the Annexin A5 may not be administered distal from the or each joint to be treated.

The skilled person is readily able to determine a suitable dosage in order to achieve the therapeutic effect desired. For example, a suitable dosage will be typically provide and maintain an adequate amount of Annexin A5 protein to treat or prevent osteoarthritis, or an associated condition.

A suitable dosage may aim to achieve and/or maintain a level of Annexin A5 protein in the blood plasma of the subject at greater that naturally-occurring physiological levels of Annexin A5 in the blood plasma, such as up to 1000 µg/ml, for example, within the range of from 5 to 900 µg/ml, from 10 to 600 µg/ml, from 20 to 500 µg/ml or 30 to 40 µg/ml. A plasma level of about from 32 to 38 µg/ml or about from 34 to 36 µg/ml may be suitable.

A suitable dosage may aim to achieve and/or maintain a level of Annexin A5 protein in the joint of the subject at greater than naturally-occurring physiological levels of Annexin A5 in the or each joint, such as at a level that is about, up to, or greater than 5%, 10%, 20%, 30%, 40%, 50%, 60%, 70%, 80%, 90% or 100% higher than naturally-occurring physiological levels of Annexin A5 in the or each joint, for example as at a level that is about, up to, or greater than 2-fold, 3-fold, 4-fold, 5-fold, 6-fold, 7-fold, 8-fold, 9-fold, 10-fold, 20-fold, 30-fold, 40-fold, 50-fold, 100-fold or more higher than naturally-occurring physiological levels of Annexin A5 in the or each joint.

A suitable dosage may aim to achieve and/or maintain a level of Annexin A5 protein in the synovial fluid of the subject at greater that naturally-occurring physiological levels of Annexin A5 in the synovial fluid in the or each joint, such as at a level that is about, up to, or greater than 5%, 10%, 20%, 30%, 40%, 50%, 60%, 70%, 80%, 90% or 100% higher than naturally-occurring physiological levels of Annexin A5 in the synovial fluid in the or each joint, for example as at a level that is about, up to, or greater than 2-fold, 3-fold, 4-fold, 5-fold, 6-fold, 7-fold, 8-fold, 9-fold, 10-fold, 20-fold, 30-fold, 40-fold, 50-fold, 100-fold or more higher than naturally-occurring physiological levels of Annexin A5 in the synovial fluid in the or each joint.

The treatment regime may, for example, involve the administration of the Annexin A5 protein in a manner that provides for prolonged blood clearance of the protein in the subject, for example where the half-life of the protein in circulation of the subject is at least about 30 minutes, at least about 1 hour, at least about 1.5 hours, at least about 2 hours, at least about 2.5 hours, at least about 3 hours or more. In some embodiments the manner of administration is intraperitoneal injection, or osmotic pump. In other embodiments the route of administration is intra-venous or intra-joint injection over an extended period of time, for example where a daily dosage as described above is delivered over a period of up to 30 minutes, up to one hour, up to 2 hours, up to 4 hours, up to 6 hours, up to 8 hours, up to 12 hours, up to 16 hours, or up to 24 hours.

The treatment regime may, for example, involve the administration of the Annexin A5 protein in a manner that provides for prolonged joint clearance or prolonged synovial fluid clearance of the protein in the subject, for example where the half-life of the protein is up to 30 minutes, up to 1 hour, up to 2 hours, up to 4 hours, up to 6 hours, up to 8 hours, up to 12 hours, up to 16 hours, up to 24 hours, up to 2 days, up to 3 days, up to 4 days, up to 5 days, up to 6 days, up to 7 days, up to 2 weeks, up to 3 weeks, up to 4 weeks, up to 2 months, up to 3 months, up to 4 months, up to 5 months, up to 6 months, up to 7 months, up to 8 months, up to 9 months, up to 10 months, up to 11 months, up to 12 months, up to 2 years, up to 3 years, up to 4 years, up to 5 years, up to 6 years, up to 7 years up to 8 years, up to 9 years, or up to 10 years.

In one preferred embodiment, the half-life of the protein in the joint is up to, or at least, about 24 hours and/or the half-life of the protein in the synovial fluid is up to, or at least, about 24 hours.

The treatment regime may, for example, involve the administration of the Annexin A5 protein in a manner that provides for prolonged joint clearance and/or prolonged synovial fluid clearance of the protein in the subject, for example where the protein is present or detectable in the joint or synovial fluid for up to 30 minutes, up to 1 hour, up to 2 hours, up to 4 hours, up to 6 hours, up to 8 hours, up to 12 hours, up to 16 hours, up to 24 hours, up to 2 days, up to 3 days, up to 4 days, up to 5 days, up to 6 days, up to 7 days, up to 2 weeks, up to 3 weeks, up to 4 weeks, up to 2 months, up to 3 months, up to 4 months, up to 5 months, up to 6 months, up to 7 months, up to 8 months, up to 9 months, up to 10 months, up to 11 months, up to 12 months, up to 2 years, up to 3 years, up to 4 years, up to 5 years, up to 6 years, up to 7 years up to 8 years, up to 9 years, or up to 10 years.

For example, in one option, the protein may be present or detectable in the joint for up to, or at least, about 24 hours and/or in the synovial fluid for up to, or at least, about 24 hours.

The administration of a therapeutically effective dose of the Annexin A5 protein can be achieved in a number of different ways. Suitable administration of a therapeutically effective dose can entail administration of a single dose, or can entail administration of doses daily, semi-weekly, weekly, once every two weeks, once a month, annually, etc.

The treatment regime may, for example, involve the continuous infusion of Annexin A5 protein to the subject, or can involve one or more administrations, for example, once, twice, three, four or more times daily. For example, administration of Annexin A5 protein twice daily may be one suitable regime and a dosage amount at each administration in the range of from about 0.1 to 25 mg/kg patient body weight, such as from about 1 to 20 mg/kg, about 5 to 20 mg/kg, about 10 to 15 mg/kg, such as about 11 mg/kg, about 12 mg/kg, about 13 mg/kg or about 14 mg/kg may be one suitable dosage regime.

In one embodiment, the Annexin A5 protein may be administered at a concentration of at least about 1 µg (micro gram)/ml: for example, at least about 2 µg/ml; at least about 3 µg/ml; at least about 4 µg/ml; at least about 5 µg/ml; at least about 6 µg/ml; at least about 7 µg/ml; at least about 8 µg/ml; at least about 9 µg/ml; at least about 10 µg/ml; at least about 11 µg/ml; at least about 12 µg/ml; at least about 13 µg/ml; at least about 14 µg/ml; at least about 15 µg/ml; at least about 16 µg/ml; at least about 17 µg/ml; at least about 18 µg/ml; at least about 19 µg/ml; at least about 20 µg/ml; at least about 21 µg/ml; at least about 22 µg/ml; at least about 23 µg/ml; at least about 24 µg/ml; at least about 25 µg/ml; at least about 26 µg/ml; at least about 27 µg/ml; at least about 28 µg/ml; at least about 29 µg/ml; at least about 30 µg/ml; at least about 31 µg/ml; at least about 32 µg/ml; at least about 33 µg/ml; at least about 34 µg/ml; at least about 35 µg/ml; at least about 36 µg/ml; at least about 37 µg/ml; at least about 38 µg/ml; at least about 39 µg/ml; at least about 40 µg/ml; at least about 41 µg/ml; at least about 42 µg/ml; at least about 43 µg/ml; at least about 44 µg/ml; at least about 45 µg/ml; at least about 46 µg/ml; at least about 47 µg/ml; at least about 48 µg/ml; at least about 49 µg/ml; at least about 50 µg/ml; at least about 55 µg/ml; at least about 60 µg/ml; at least about 65 µg/ml; at least about 70 µg/ml; at least about 75 µg/ml; at least about 80 µg/ml; at least about 85 µg/ml; at least about 90 µg/ml; at least about 95 µg/ml; at least about 100 µg/ml; at least about 110 µg/ml; at least about 120 µg/ml; at least about 130 µg/ml; at least about 140 µg/ml; at least about 150 µg/ml; at least about 160 µg/ml; at least about 170 µg/ml; at least about 180 µg/ml; at least about 190 µg/ml; at least about 200 µg/ml; at least about 210 µg/ml; at least about 220 µg/ml; at least about 230 µg/ml; at least about 240 µg/ml; at least about 250 µg/ml; at least about 260 µg/ml; at least about 270 µg/ml; at least about 280 µg/ml; at least about 290 µg/ml; at least about 300 µg/ml; at least about 350 µg/ml; at least about 400 µg/ml; at least about 450 µg/ml; or at least about 500 µg/ml.

In one embodiment, the Annexin A5 protein may be administered into the or each joint and/or into the synovial fluid in the or each joint, at a concentration of at least about 1 µg (micro gram)/ml: for example, at least about 2 µg/ml; at least about 3 µg/ml; at least about 4 µg/ml; at least about 5 µg/ml; at least about 6 µg/ml; at least about 7 µg/ml; at least about 8 µg/ml; at least about 9 µg/ml; at least about 10 µg/ml; at least about 11 µg/ml; at least about 12 µg/ml; at least about 13 µg/ml; at least about 14 µg/ml; at least about 15 µg/ml; at least about 16 µg/ml; at least about 17 µg/ml; at least about 18 µg/ml; at least about 19 µg/ml; at least about 20 µg/ml; at least about 21 µg/ml; at least about 22 µg/ml; at least about 23 µg/ml; at least about 24 µg/ml; at least about 25 µg/ml; at least about 26 µg/ml; at least about 27 µg/ml; at least about 28 µg/ml; at least about 29 µg/ml; at least about 30 µg/ml; at least about 31 µg/ml; at least about 32 µg/ml; at least about 33 µg/ml; at least about 34 µg/ml; at least about 35 µg/ml; at least about 36 µg/ml; at least about 37 µg/ml; at least about 38 µg/ml; at least about 39 µg/ml; at least about 40 µg/ml; at least about 41 µg/ml; at least about 42 µg/ml; at least about 43 µg/ml; at least about 44 µg/ml; at least about 45 µg/ml; at least about 46 µg/ml; at least about 47 µg/ml; at least about 48 µg/ml; at least about 49 µg/ml; at least about 50 µg/ml; at least about 55 µg/ml; at least about 60 µg/ml; at least about 65 µg/ml; at least about 70 µg/ml; at least about 75 µg/ml; at least about 80 µg/ml; at least about 85 µg/ml; at least about 90 µg/ml; at least about 95 µg/ml; at least about 100 µg/ml; at least about 110 µg/ml; at least about 120 µg/ml; at least about 130 µg/ml; at least about 140 µg/ml; at least about 150 µg/ml; at least about 160 µg/ml; at least about 170 µg/ml; at least about 180 µg/ml; at least about 190 µg/ml; at least about 200 µg/ml; at least about 210 µg/ml; at least about 220 µg/ml; at least about 230 µg/ml; at least about 240 µg/ml; at least about 250 µg/ml; at least about 260 µg/ml; at least about 270 µg/ml; at least about 280 µg/ml; at least about 290 µg/ml; at least about 300 µg/ml; at least about 350 µg/ml; at least about 400 µg/ml; at least about 450 µg/ml; or at least about 500 µg/ml.

In one embodiment, the Annexin A5 protein is administered into the or each joint at a concentration of about 1 µg/ml.

In another embodiment, the Annexin A5 protein is administered into the joint at a concentration of about 5 µg/ml.

In another embodiment, the Annexin A5 protein is administered into the joint at a concentration of about 17 µg/ml.

In another embodiment, the Annexin A5 protein is administered into the joint at a concentration of about 20 µg/ml.

In another embodiment, the Annexin A5 protein is administered into the joint at a concentration of about 174 µg/ml.

In another embodiment, the Annexin A5 protein is administered into the joint at a concentration of about 200 µg/ml.

Total doses of Annexin A5 per administration may be in the region of for example, 0.0001 to 3 g, 0.0001 to 1.75 g, 0.001 to 3 g, 0.001 to 1.75 g, 0.01 to 3 g, 0.01 to 1.75 g, 0.1 to 3 g, or 0.1 to 1.75 g, such as 0.2 to 2 g, 0.5 to 1.5 g, 0.8 to 1.2 g or about 1 g of Annexin A5. In one embodiment, total doses of Annexin A5 per systemic administration may be in the region of for example, 0.01 to 3 g, 0.01 to 1.75 g, 0.1 to 3 g, or 0.1 to 1.75 g, such as 0.2 to 2 g, 0.5 to 1.5 g, 0.8 to 1.2 g or about 1 g of Annexin A5. In one embodiment, total doses of Annexin A5 per joint administration may be in the region of for example, 0.0001 to 1 g, 0.0001 to 0.5 g, 0.001 to 1 g, or 0.001 to 0.5 g, such as about 0.0001 g, about 0.0005 g, about 0.001 g, about 0.005 g, about 0.01 g, about 0.05 g, about 0.1 g, about 0.5 g, or about 1 g of Annexin A5.

In one embodiment, the Annexin A5 protein or composition may be administered into the or each joint at a volume which is at least about 1% of the joint volume: for example, at least about 2% of the or each joint volume; at least about 3% of the or each joint volume; at least about 4% of the or each joint volume; at least about 5% of the or each joint volume; at least about 6% of the or each joint volume; at least about 7% of the or each joint volume; at least about 8% of the or each joint volume; at least about 9% of the or each joint volume; at least about 10% of the or each joint volume; at least about 11% of the or each joint volume; at least about 12% of the or each joint volume; at least about 13% of the or each joint volume; at least about 14% of the or each joint volume; at least about 15% of the or each joint volume; at least about 16% of the or each joint volume; at least about 17% of the or each joint volume; at least about 18% of the or each joint volume; at least about 19% of the or each joint volume; at least about 20% of the or each joint volume; at least about 21% of the or each joint volume; at least about 22% of the or each joint volume; at least about 23% of the or each joint volume; at least about 24% of the or each joint volume; at least about 25% of the or each joint volume; at least about 26% of the or each joint volume; at least about 27% of the or each joint volume; at least about 28% of the or each joint volume; at least about 29% of the or each joint volume; at least about 30% of the or each joint volume; at least about 35% of the or each joint volume; at least about 40% of the or each joint volume; at least about 45% of the or each joint volume; at least about 50% of the or each joint volume; at least about 55% of the or each joint volume; at least about 60% of the or each joint volume; at least about 65% of the or each joint volume; at least about 70% of the or each joint volume; at least about 75% of the or each joint volume; at least about 80% of the or each joint volume; at least about 85% of the or each joint volume; at least about 90% of the or each joint volume; at least about 95% of the or each joint volume; or at least about 100% of the or each joint volume.

Preferably, the Annexin A5 protein or composition is administered into the or each joint at a volume which is about 17% of the or each joint volume; about 17.1% of the or each joint volume; about 17.2% of the or each joint volume; about 17.3% of the or each joint volume; about 17.4% of the or each joint volume; about 17.5% of the or each joint volume; about 17.6% of the or each joint volume; about 17.7% of the or each joint volume; about 17.8% of the or each joint volume; about 17.9% of the or each joint volume; or about 18% of the or each joint volume.

In one preferred embodiment, the Annexin A5 protein or composition is administered into the or each joint at a volume which is about 17.1% of the or each joint volume.

In another preferred embodiment, the Annexin A5 protein or composition is administered into the or each joint at a volume which is about 17.4% of the or each joint volume.

In another preferred embodiment, the Annexin A5 protein or composition is administered into the or each joint at a volume which is about 17.8% of the or each joint volume.

In one embodiment, the Annexin A5 protein or composition may be administered into the joint or each at a volume which is at least about 1% of the synovial volume: for example, at least about 2% of the synovial volume; at least about 3% of the synovial volume; at least about 4% of the synovial volume; at least about 5% of the synovial volume; at least about 6% of the synovial volume; at least about 7% of the synovial volume; at least about 8% of the synovial volume; at least about 9% of the synovial volume; at least about 10% of the synovial volume; at least about 11% of the synovial volume; at least about 12% of the synovial volume; at least about 13% of the synovial volume; at least about 14% of the synovial volume; at least about 15% of the synovial volume; at least about 16% of the synovial volume; at least about 17% of the synovial volume; at least about 18% of the synovial volume; at least about 19% of the synovial volume; at least about 20% of the synovial volume; at least about 21% of the synovial volume; at least about 22% of the synovial volume; at least about 23% of the synovial volume; at least about 24% of the synovial volume; at least about 25% of the synovial volume; at least about 26% of the synovial volume; at least about 27% of the synovial volume; at least about 28% of the synovial volume; at least about 29% of the synovial volume; at least about 30% of the synovial volume; at least about 35% of the synovial volume; at least about 40% of the synovial volume; at least about 45% of the synovial volume; at least about 50% of the synovial volume; at least about 55% of the synovial volume; at least about 60% of the joint synovial volume; at least about 65% of the synovial volume; at least about 70% of the synovial volume; at least about 75% of the synovial volume; at least about 80% of the synovial volume; at least about 85% of the synovial volume; at least about 90% of the synovial volume; at least about 95% of the synovial volume; or at least about 100% of the synovial volume in the or each joint.

Preferably, the Annexin A5 protein or composition is administered into the or each joint at a volume which is about 17% of the synovial volume; about 17.1% of the synovial volume; about 17.2% of the synovial volume; about 17.3% of the synovial volume; about 17.4% of the synovial volume; about 17.5% of the synovial volume; about 17.6% of the synovial volume; about 17.7% of the synovial volume; about 17.8% of the synovial volume; about 17.9% of the synovial volume; or about 18% of the synovial volume in the or each joint.

In one preferred embodiment, the Annexin A5 protein or composition is administered into the or each joint at a volume which is about 17.1% of the synovial volume in the or each joint.

In another preferred embodiment, the Annexin A5 protein or composition is administered into the or each joint at a volume which is about 17.4% of the synovial volume in the or each joint.

In another preferred embodiment, the Annexin A5 protein or composition is administered into the or each joint at a volume which is about 17.8% of the synovial volume in the or each joint.

In one embodiment, the Annexin A5 protein or composition may be administered into the or each joint at a volume which is at least about 0.1 ml: for example, at least about 0.2 ml, at least about 0.3 ml, at least about 0.4 ml, at least about 0.5 ml, at least about 0.6 ml, at least about 0.7 ml, at least about 0.8 ml, at least about 0.9 ml, at least about 1 ml, at least about 1.1 ml; at least about 1.2 ml, at least about 1.3 ml, at least about 1.4 ml, at least about 1.5 ml, at least about 1.6 ml, at least about 1.7 ml, at least about 1.8 ml, at least about 1.9 ml, at least about 2 ml, at least about 2.1 ml, at least about 2.2 ml, at least about 2.3 ml, at least about 2.4 ml, at least about 2.5 ml, at least about 2.6 ml, at least about 2.7 ml, at least about 2.8 ml, at least about 2.9 ml, at least about 3 ml, at least about 3.1 ml, at least about 3.2 ml, at least about 3.3 ml, at least about 3.4 ml, at least about 3.5 ml, at least about 3.6 ml, at least about 3.7 ml, at least about 3.8 ml, at least about 3.9 ml, at least about 4 ml, at least about 4.1 ml, at least about 4.2 ml, at least about 4.3 ml, at least about 4.4 ml, at least about 4.5 ml, at least about 4.6 ml, at least about 4.7 ml, at least about 4.8 ml, at least about 4.9 ml, at least about 5 ml, at least about 6 ml, at least about 7 ml, at least about 8 ml, at least about 9 ml, at least about 10 ml, at least about 11 ml, at least about 12 ml, at least about 13 ml, at least about 14 ml, at least about 15 ml, at least about 16 ml, at least about 17 ml, at least about 18 ml, at least about 19 ml, at least about 20 ml, at least about 25 ml, at least about 30 ml, at least about 35 ml, or at least about 40 ml.

In one preferred embodiment, the Annexin A5 protein or composition is administered into the or each joint (preferably the joints of the fingers, including joints of the hand, or the joints of the toes, including articulations of the foot, most preferably in a human subject) at a volume of about 1 ml.

In another preferred embodiment, the Annexin A5 protein or composition is administered into the or each joint (preferably the wrist joint or the thumb joint, most preferably in a human subject) at a volume of about 2 ml.

In another preferred embodiment, the Annexin A5 protein or composition is administered into the or each joint at a volume of about 4 ml.

In another preferred embodiment, the Annexin A5 protein or composition is administered into the or each joint (preferably the elbow joint or the hip joint, most preferably in a human subject) at a volume of about 5 ml.

In another preferred embodiment, the Annexin A5 protein or composition is administered into the or each joint at a volume of about 6 ml.

In another preferred embodiment, the Annexin A5 protein or composition is administered into the or each joint (preferably the shoulder joint or the knee joint, most preferably in a human subject) at a volume of about 10 ml.

The term "about" in this context includes the meaning of ±2 ml, 1.5 ml. 1 ml, 0.5 ml or 0.1 ml pf the stated volume.

In some cases, a therapeutically effective dose is administered to the subject as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose, and each subsequent dose can be increased by a particular increment (e.g., by 0.5 mg/kg), or by variable increments, until a therapeutic dose is reached, at which point administration may cease or may continue (e.g., continued therapeutic doses). In some embodiments, administration of a therapeutically effective dose can be a continuous infusion and the dose can altered (e.g., escalated) over time. In some embodiments a combination therapy is also administered.

Dosage and frequency may vary depending on the half-life of the Annexin A5 protein in the subject.

The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

For veterinary use, the Annexin A5 protein is administered as a suitably acceptable formulation in accordance with normal veterinary practice and the veterinary surgeon will determine the dosing regimen and route of administration which will be most appropriate for a particular animal.

Treatment Periods:

The treatment regime may be continued for a therapeutically beneficial period.

Osteoarthritis is a generally considered to be a chronic disease, so it might be necessary for treatment to be continued for the remaining life of the subject. Osteoarthritis is also a disease which is more likely to affect older subjects than younger subjects, as discussed in the foregoing.

In one embodiment, the Annexin A5 protein may be administered to the subject from when the subject is diagnosed with osteoarthritis until the death of the subject.

Preferably, the subject is an elderly subject and the Annexin A5 protein is administered to the subject from when the subject is diagnosed with osteoarthritis until the death of the subject.

In one embodiment, the Annexin A5 protein may be administered to the subject from when the subject is diagnosed with osteoarthritis until the subject is no longer diagnosed with osteoarthritis.

In another embodiment, the Annexin A5 protein may be administered to the subject for prophylaxis in advance of a diagnosis with osteoarthritis, for example in the case of a subject who leads a high risk lifestyle (such as athletes, racehorses, etc.) and/or in the case of a subject with a family history of osteoarthritis.

In one embodiment, the Annexin A5 protein is administered for a period of one week or more: for example, two weeks or more; three weeks or more; four weeks or more; two months or more; three months or more; four months or more; five months or more; six months or more; seven months or more; eight months or more; nine months or more; ten months or more; 11 months or more; 12 months or more; 15 months or more; 18 months or more; 21 months or more; 24 months or more; 30 months or more; three years or more; 42 months or more; four years or more; five years or more; six years or more; seven years or more; eight years or more; nine years or more; ten years of more; 11 years or more; 12 years or more; 13 years or more; 14 years or more; 15 years or more; 16 years or more; 17 years or more; 18 years or more; 19 years or more; 20 years or more; 25 years or more; 30 years or more; 35 years or more; 40 years or more; or 50 years or more.

In one embodiment, the Annexin A5 protein is administered once weekly for a period of one week or more: for example, two weeks or more; three weeks or more; four weeks or more; two months or more; three months or more; four months or more; five months or more; six months or more; seven months or more; eight months or more; nine months or more; ten months or more; 11 months or more; 12 months or more; 15 months or more; 18 months or more; 21 months or more; 24 months or more; 30 months or more; three years or more; 42 months or more; four years or more; five years or more; six years or more; seven years or more; eight years or more; nine years or more; ten years of more; 11 years or more; 12 years or more; 13 years or more; 14 years or more; 15 years or more; 16 years or more; 17 years or more; 18 years or more; 19 years or more; 20 years or more; 25 years or more; 30 years or more; 35 years or more; 40 years or more; or 50 years or more.

In one embodiment, the Annexin A5 protein is administered twice weekly for a period of one week or more: for example, two weeks or more; three weeks or more; four weeks or more; two months or more; three months or more; four months or more; five months or more; six months or more; seven months or more; eight months or more; nine months or more; ten months or more; 11 months or more; 12 months or more; 15 months or more; 18 months or more; 21 months or more; 24 months or more; 30 months or more; three years or more; 42 months or more; four years or more; five years or more; six years or more; seven years or more; eight years or more; nine years or more; ten years of more; 11 years or more; 12 years or more; 13 years or more; 14 years or more; 15 years or more; 16 years or more; 17 years or more; 18 years or more; 19 years or more; 20 years or more; 25 years or more; 30 years or more; 35 years or more; 40 years or more; or 50 years or more.

In one embodiment, the Annexin A5 protein is administered once monthly for a period of one month or more: for example, two months or more; three months or more; four months or more; five months or more; six months or more; seven months or more; eight months or more; nine months or more; ten months or more; 11 months or more; 12 months or more; 15 months or more; 18 months or more; 21 months or more; 24 months or more; 30 months or more; three years or more; 42 months or more; four years or more; five years or more; six years or more; seven years or more; eight years or more; nine years or more; ten years of more; 11 years or more; 12 years or more; 13 years or more; 14 years or more; 15 years or more; 16 years or more; 17 years or more; 18 years or more; 19 years or more; 20 years or more; 25 years or more; 30 years or more; 35 years or more; 40 years or more; or 50 years or more.

In one embodiment, the Annexin A5 protein is administered twice monthly for a period of one month or more: for example, two months or more; three months or more; four months or more; five months or more; six months or more; seven months or more; eight months or more; nine months or more; ten months or more; 11 months or more; 12 months or more; 15 months or more; 18 months or more; 21 months or more; 24 months or more; 30 months or more; three years or more; 42 months or more; four years or more; five years or more; six years or more; seven years or more; eight years or more; nine years or more; ten years of more; 11 years or more; 12 years or more; 13 years or more; 14 years or more; 15 years or more; 16 years or more; 17 years or more; 18 years or more; 19 years or more; 20 years or more; 25 years or more; 30 years or more; 35 years or more; 40 years or more; or 50 years or more.

Administrative Routes:

Any suitable route of administration may be used, although parenteral, including injection (such as intravenous, subcutaneous or intramuscular injection), infusion (such as intravenous infusion) and/or by intrathecal delivery to avoid the blood brain barrier, may be particularly suitable.

Optionally, the Annexin A5 protein can be administered parenterally, intravenously, intrathecally, intra-arterially, intra-peritoneally, intra jointly. intra-muscularly, or subcutaneously or locally.

Most preferably, the Annexin A5 protein is administered directly into the or each joint and/or into the synovial fluid within the or each joint, as discussed above.

Combination Therapies:

A subject for treatment in accordance with the present invention can be administered Annexin A5 in an amount and for a time to provide an overall therapeutic effect. The Annexin A5 can be administered alone (monotherapy) or in combination with other agents (combination therapy), either in admixture or by separate, simultaneous or sequential administration. In the case of a combination therapy, the amounts and times of administration can be those that provide, e.g., an additive or a synergistic therapeutic effect. Further, the administration of the Annexin A5 (with or without the second or further agent(s)) can be used as a primary, e.g., first line treatment, or as a secondary treatment, e.g., for subjects who have an inadequate response to a previously administered therapy (i.e., a therapy other than one with an Annexin A5).

Accordingly, in one embodiment, the subject may be treated with the Annexin A5 protein therapy in addition to one or more therapeutic or prophylactic interventions. The subject may receive the Annexin A5 protein therapy in the same composition as, separately from, simultaneously with a separate formulation containing, or sequentially with, one or more other therapeutic or prophylactic interventions, or one or more additional therapeutic or prophylactic treatments.

Preferably, the one or more additional therapeutic or prophylactic treatments may be selected from one or more of: lifestyle changes; medication; and surgery.

Preferably, the lifestyle changes may be weight loss or exercise.

Preferably, the medication may be one or more of the following: pain mediation (i.e. medication to relieve a symptom of pain); antacid; non-steroidal anti-inflammatory drugs (NSAIDs); capsaicin; and hyaluronic acid.

Preferably, the pain medication is one of more of the following: acetaminophen; paracetamol; Ibuprofen; aspirin; an opiod (such as tramadol); and a glucocorticoid (such as hydrocortisone).

Preferably, the NSAID is one of more of the following: naproxen; diclofenac; and COX-2 selective inhibitors (such as celecoxib).

Preferably, the surgery is one or more of the following: joint replacement (such as hip replacement and knee replacement); osteotomy; and arthroscopic surgery.

Devices and Kits for Therapy:

Pharmaceutical and veterinary compositions that include the Annexin A5 protein can be administered with a medical device. The device can designed with features such as portability, room temperature storage, and ease of use so that it can be used in emergency situations, e.g., by an untrained subject or by emergency personnel in the field, removed from medical facilities and other medical equipment. The device can include, e.g., one or more housings for storing pharmaceutical preparations that include the Annexin A5 protein, and can be configured to deliver one or more unit doses of the Annexin A5 protein. The device can be further configured to administer a second agent, either as a single pharmaceutical composition that also includes the Annexin A5 or as two separate compositions.

The pharmaceutical and veterinary composition may be administered with a syringe. The pharmaceutical or veterinary composition can also be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

The Annexin A5 protein can be provided in a kit. In one embodiment, the kit includes (a) a container that contains a composition that includes the Annexin A5 protein, and optionally (b) informational material. The informational material can be descriptive, instructional, marketing or other material that relates to the methods described herein and/or the use of the agents for therapeutic benefit.

In an embodiment, the kit also includes a second agent for treating a disorder described herein. For example, the kit includes a first container that contains a composition that includes the Annexin A5 protein, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the Annexin A5 protein, e.g., in a suitable dose, dosage form, or mode of administration (e.g., a dose, dosage form, or mode of administration described herein), to treat a subject in need thereof as described herein. The information can be provided in a variety of formats, include printed text, computer readable material, video recording, or audio recording, or information that provides a link or address to substantive material, e.g., on the internet.

In addition to the Annexin A5 protein, the composition in the kit can include other ingredients, such as a solvent or buffer, a stabilizer, or a preservative. The Annexin A5 protein can be provided in any form, e.g., liquid, dried or lyophilized form, preferably substantially pure and/or sterile. When the Annexin A5 protein is provided in a liquid solution, the liquid solution preferably is an aqueous solution. When the Annexin A5 protein is provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the Annexin A5 protein and a second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

F. Treatment of Inflammation in a Joint

Previously, platelet-rich plasma (PRP) has been used to treat joint inflammation. However, the mechanism by which it works has not been understood. The method involves concentrating platelets from a patient's plasma, and then reintroducing those concentrated platelets into the same patient, reducing inflammation. The applicant has found that PRP possesses substantially higher Annexin A5 levels than regular plasma. Annexin A5 protein is postulated to be the active component of PRP, so is described herewith as a therapeutic agent for treating joint inflammation in general.

In a fifth aspect, the present invention provides Annexin A5 protein for use in the prophylaxis or the treatment of inflammation in one or more joints, in a subject.

In an alternative embodiment of the fifth aspect, the present invention provides a method for the prophylaxis or the treatment of inflammation in one or more joints, in a subject;
wherein the method comprises the step of administering a therapeutically effective amount of the Annexin A5 protein to the subject.

In another alternative embodiment of the fifth aspect, the present invention provides for the use of Annexin A5 protein in the manufacture of a medicament for the prophylaxis or the treatment of inflammation in one or more joints, in a subject.

In one embodiment, the inflammation is caused by an inflammatory disease.

In one embodiment, the inflammatory disease is selected from the listing consisting of: arthritis; lupus erythematosus, polymyositis, dermatomyositis, Sjögren's syndrome, scleroderma; mixed connective tissue disease; Osgood-Schlatter's disease; viral hepatitis; rubella; Behçet's syndrome; Henoch-Schönlein purpura; and sarcoidosis.

Preferably, the arthritis is selected from the list consisting of: rheumatoid arthritis; osteoarthritis; gout; lupus; fibromyalgia; psoriatic arthritis; reactive arthritis; juvenile arthritis; ankylosing spondylitis; and septic arthritis.

Most preferably, the arthritis is rheumatoid arthritis.

In one embodiment, the inflammation is caused by a physical injury.

In one embodiment, the physical injury is one or more selected from the list consisting of: tendonitis; bursitis; a damaged (for example, torn) ligament; a damaged (for example, torn) tendon; menisci damage; cartilage damage; a sprain; a broken bone; a fractured bone; a chipped bone; a dislocation of a bone; and tenosynovitis.

In further embodiments of the fifth aspect of the invention are included the embodiments and preferable features disclosed above in respect of the first to fourth aspects of the invention. For example, it is included that the or each joint referred to in the fifth aspect of the invention can be described as disclosed in section B. Likewise, the Annexin A5 protein referred to in the fifth aspect of the invention can be described as disclosed in section C, the subject referred to in the fifth aspect of the invention can be described as disclosed in section D, and/or the modes of administration, dosages and the like can be described as disclosed in section E and so on.

The present invention will now be described with reference to one or more non-limiting examples.

EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods:

Chondrocyte cells derived from a patient with osteoarthritis (OA) were cultured with IL1 β (10 ng/mL) or TNF α (10 ng/mL) and with/without Annexin A5 (ANXA5) (100 ng/mL, 5 µg/mL, 20 µg/mL). The stimulation of the chondrocytes with IL1 β or TNF α models an inflamed joint environment. Cells were harvested at 3, 6, 12 and 18 hours. The surface expression of ICAM-1 (Intercellular Adhesion Molecule 1), RANKL (Receptor activator of nuclear kappa-β ligand) and cell viability with propidium iodide (PI) were determined by flow cytometry.

Expression of inflammation-associated genes IL-6 and COX-2 was measured in IL1 β-stimulated OA chondrocytes. OA chondrocytes were stimulated with 10 ng of IL1 β and treated with different concentration of ANXA5 (0.1 µg, 5 µg and 20 µg/mL) of ANXA5 for 6 hours. Expression of genes were measured by qPCR using SYBR green reaction kit. Genes expression were normalized against GAPDH and relative expression of genes were measured using 2ΔΔCt.

Results:

A contributing factor to the osteoarthritis phenotype is cell death. The results show that treatment with Annexin A5 reduces osteoarthritis-associated cell death in ex vivo study.

FIG. 1 shows that in a human model, cell death caused by osteoarthritis (promoted by application of TNFα) is inhibited through treatment of Annexin A5, with cell viability of the Annexin A5 treated cells being similar to the control without TNFα treatment.

Figure 3:
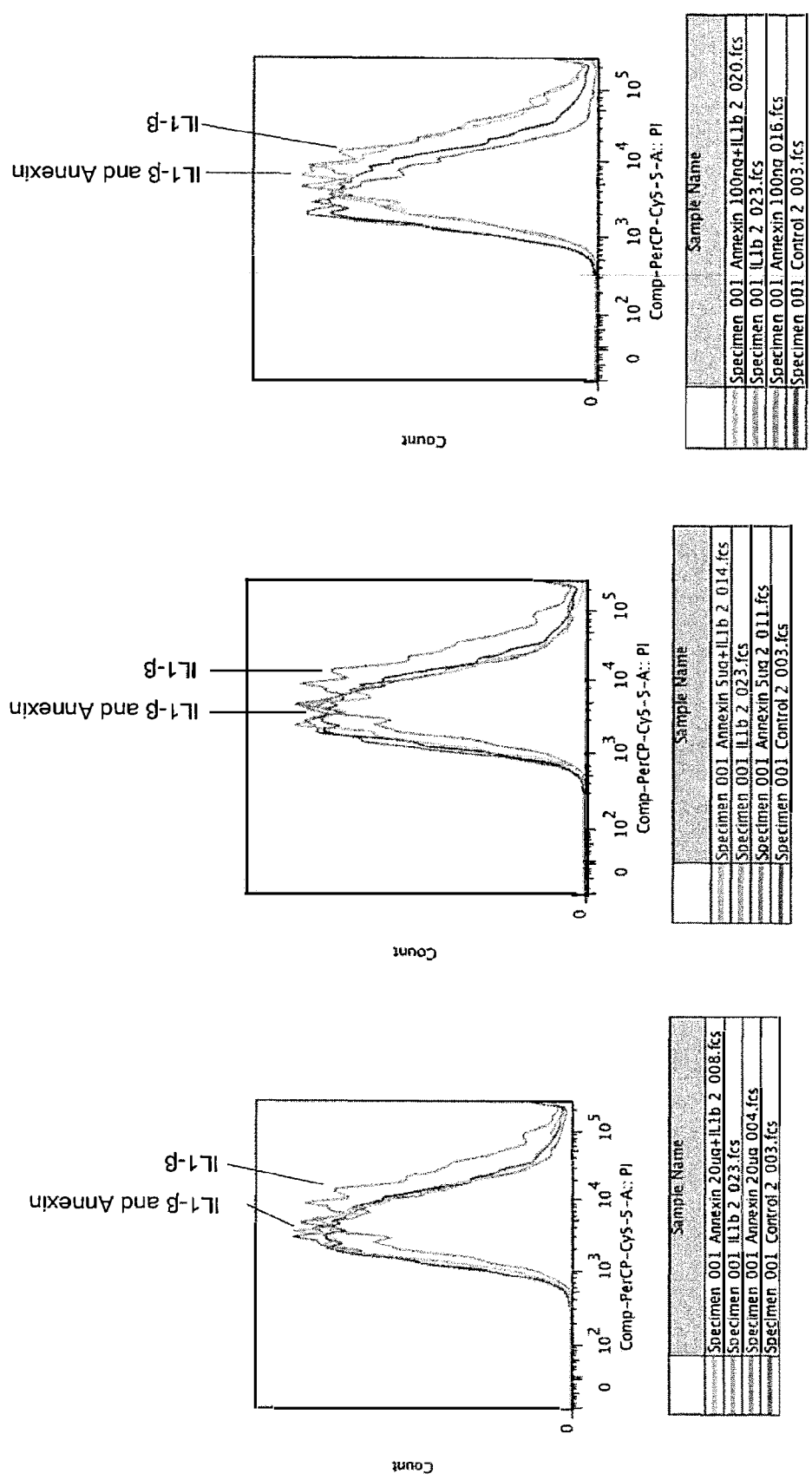
FIG. 3 shows that cell viability is increased in osteoarthritis cells on treatment with Annexin A5 protein, in a dose dependent manner. The experiment has been undertaken on a primary chondrocyte cell culture from an osteoarthritis patient, using flow cytometry. The osteoarthritis joint inflammation was mimicked in the cells through the application of IL1-β, which led to a reduction in cell viability. This is shown in the figure as for each experiment the flow cytometry curve for the sample to which only IL1-β (marked on the figure) has been applied is shifted to being the furthest curve from the y-axis, whilst the control cells to which IL1-β has not been applied are at the centre of the graph. This particular positioning of those curves shows that cell death occurs at a higher level when IL1-β has been applied. Also shown is that application of Annexin A5 protein alone at all three dosages does not cause an increase in cell death when compared to the control sample, as the control curve and the Annexin A5 protein curve for all three dosages are at the same position. Lastly, application of Annexin A5 in addition to IL1-β inhibits cell death in a dose dependent manner, with dosages of 20 µg and 5 µg exhibiting a cell viability at the same levels as observed in the control. This is shown as the flow cytometry curves for 20 µg and 5 µg dosages of Annexin A5 are at the centre of the graph (marked on the figure), in line with the control curve and the Annexin A5 protein alone curve. The 100 ng dosage also inhibits cell death but to a lesser extent, which can be seen as the 100 ng flow cytometry curve (marked on the figure) is between the middle of the graph and the IL1-β alone curve.

A similar result is seen with yet another trigger of inflammation IL1-β linked the pathogenesis of osteoarthritis in horse, as shown in FIG. 3. In a dose dependent manner, Annexin A5 is shown to inhibit osteoarthritis-associated cell death, with treatment at doses of 5 µg and 20 µg leading to cell viability comparable to the control without IL1-β treatment. Additionally, FIG. 3 shows that treatment with Annexin A5 protein alone does not affect cell viability, when compared to the control without IL1-β treatment.

As well as inhibiting osteoarthritis-associated cell death, treatment with Annexin A5 also reduces biomarkers of osteoarthritis, and osteoarthritis-associated inflammation.

Figure 2:
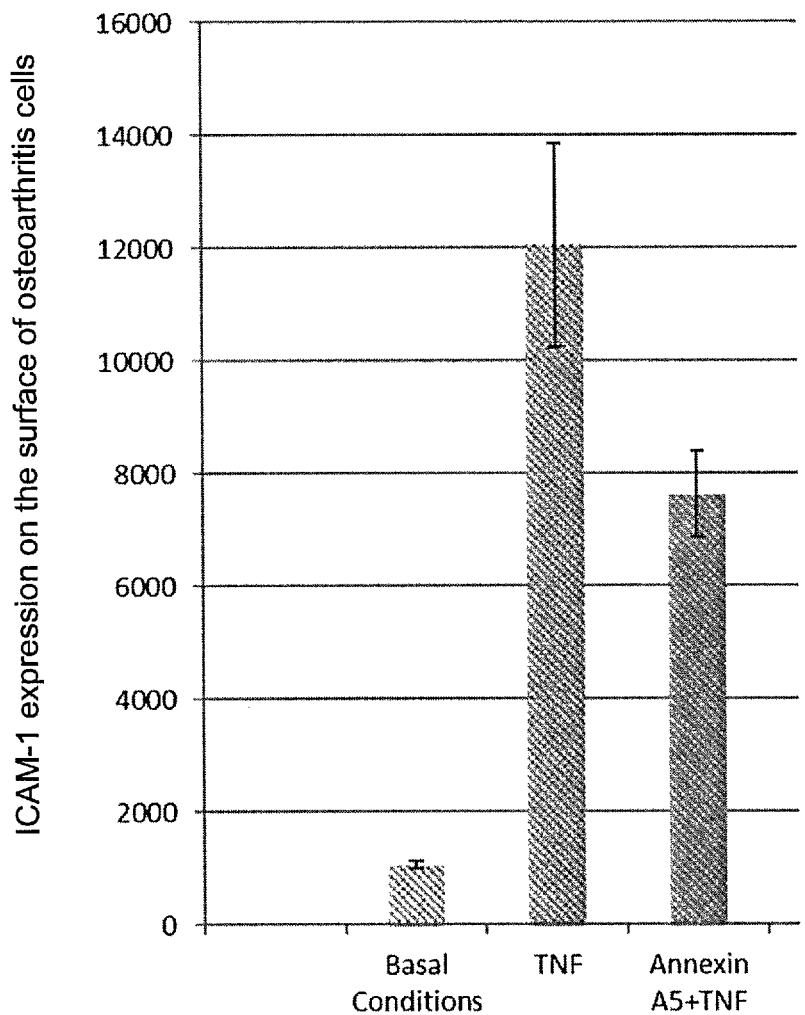
FIG. 2 shows that the expression of ICAM1, is decreased on treatment with Annexin A5. The experiment has been undertaken on a primary chondrocyte cell culture from an osteoarthritis patient using flow cytometry. The osteoarthritis joint inflammation was mimicked in the cells through the application of TNFα, which increased surface expression of ICAM1 (column two) when compared to control cells to which TNFα had not been applied (column one). Application of Annexin A5 in addition to TNFα decreased the surface expression of ICAM1 (column three).

ICAM1 is a marker of cell activation/inflammation, with relevance to osteoarthritis and chondrocytes. As shown in FIG. 2, treatment with Annexin A5 reduces the expression of ICAM1 when compared to cells in which cell death and inflammation (both hallmarks of osteoarthritis) are promoted using TNFα and the control which has not been treated with TNFα.

Figure 4:
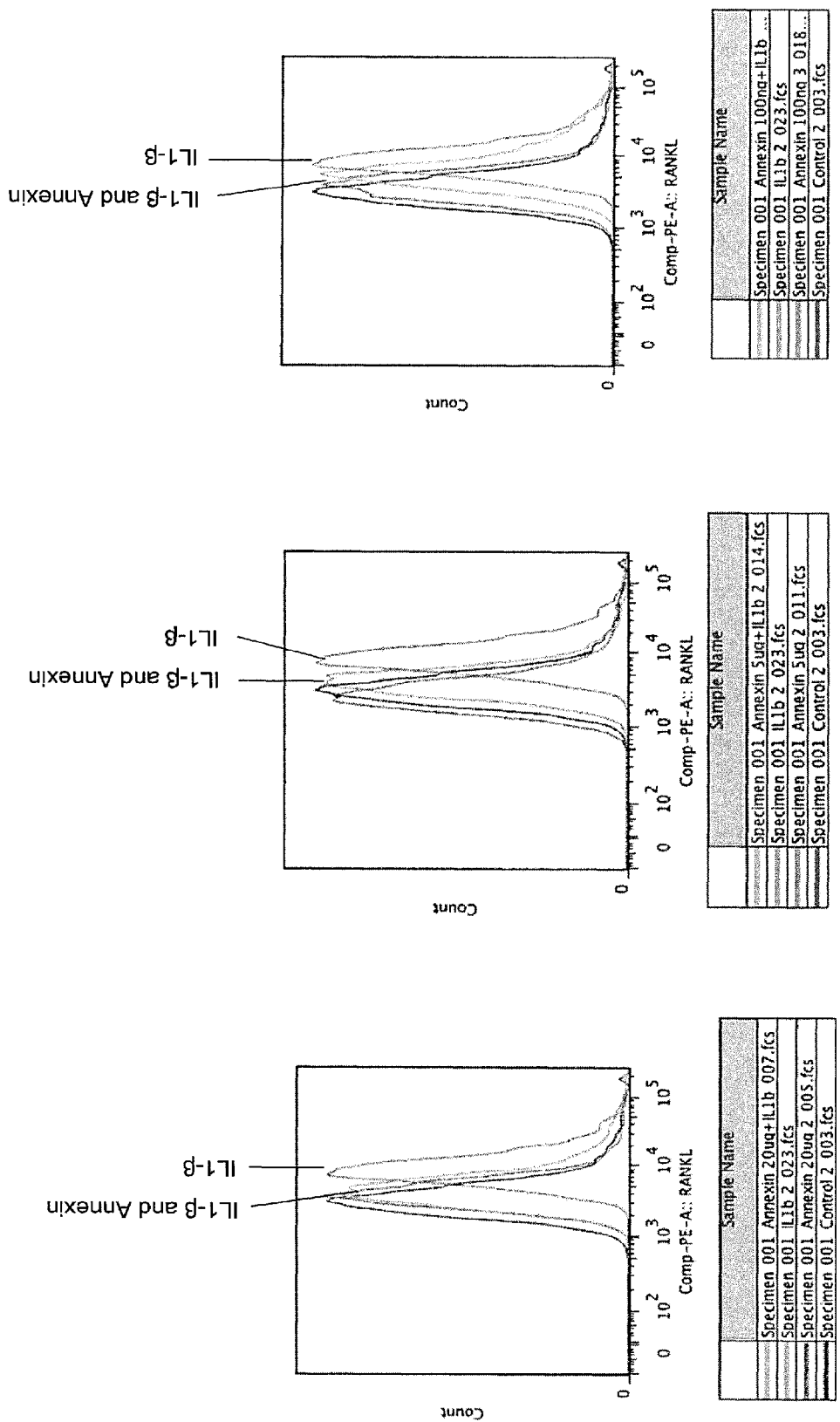
FIG. 4 shows that the expression of a marker of osteoarthritis, RANKL, is decreased on treatment with Annexin A5 protein, in a dose dependent manner. The experiment has been undertaken on a primary chondrocyte cell culture from an osteoarthritis patient, using flow cytometry. The osteoarthritis joint inflammation was mimicked in the cells through the application of IL1-β, which led to an increase in RANKL expression. This is shown in the figure as for each experiment the flow cytometry curve for the sample to which only IL1-β has been applied (marked on the figure) is shifted to being the furthest curve from the y-axis, whilst the control cells to which IL1-β has not been applied are at the centre of the graph. This particular positioning of those curves shows that RANKL is more highly expressed when IL1-β has been applied. Also shown is that application of Annexin A5 protein alone at all three dosages does not cause an increase in RANKL expression when compared to the control sample, as the control curve and the Annexin A5 protein curve for all three dosages are at the same position. Lastly, application of Annexin A5 in addition to IL1-β decreases RANKL expression in a dose dependent manner, with dosages of 20 µg and 5 µg returning RANKL expression to the same levels as observed in the control. This is shown as the flow cytometry curves for 20 µg and 5 µg dosages of Annexin A5 are at the centre of the graph (marked on the figure), in line with the control curve and the Annexin A5 protein alone curve. The 100 ng dosage also decreases RANKL expression but to a lesser extent, which can be seen as the 100 ng flow cytometry curve (marked on the figure) is between the middle of the graph and the IL1-β alone curve.

RANKL is a further marker of cell activation/inflammation, with relevance to osteoarthritis and chondrocytes. As shown in FIG. 4, treatment with Annexin A5 reduces the expression of RANKL in a dose-dependent manner, when compared to cells in which an inflamed joint model of osteoarthritis is promoted using IL1-β and the control which has not been treated with IL1-β. Treatment with Annexin A5 protein at doses of 5 μg and 20 μg leads to RANKL expression levels comparable to the control without IL1-β treatment. Additionally, FIG. 4 shows that treatment with Annexin A5 protein alone does not have an effect on RANKL expression.

Figure 5A:
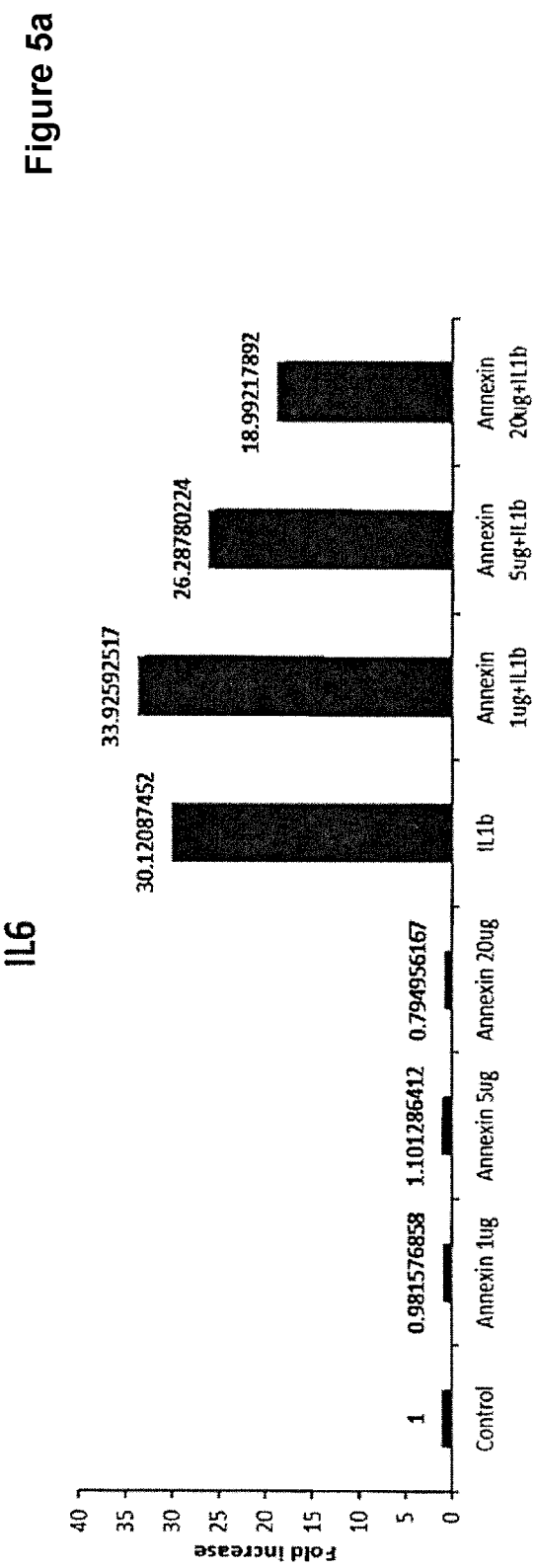
FIG. 5 shows that the expression of osteoarthritis-associated inflammation genes, IL-6 and COX-2, are decreased on treatment with Annexin A5, in a dose dependent manner. The experiment has been undertaken on a primary chondrocyte cell culture from an osteoarthritis patient with two step qPCR. The osteoarthritis joint inflammation was mimicked in the cells through the application of IL1-β, which led to an increase in IL-6 expression (FIG. 5A, column five) and COX2 expression (FIG. 5B, column five) when compared to the control samples to which IL1-β has not been applied (FIGS. 5A and 5B, column one). Application of Annexin A5 protein alone at all dosages did not increase the expression of either IL6 or COX2 (FIGS. 5A and 5B, columns one to four). Application of Annexin A5 in addition to IL1-β decreases IL-6 and COX-2 gene expression in a dose dependent manner (FIGS. 5A and 5B, columns five to eight).
Figure 5B:
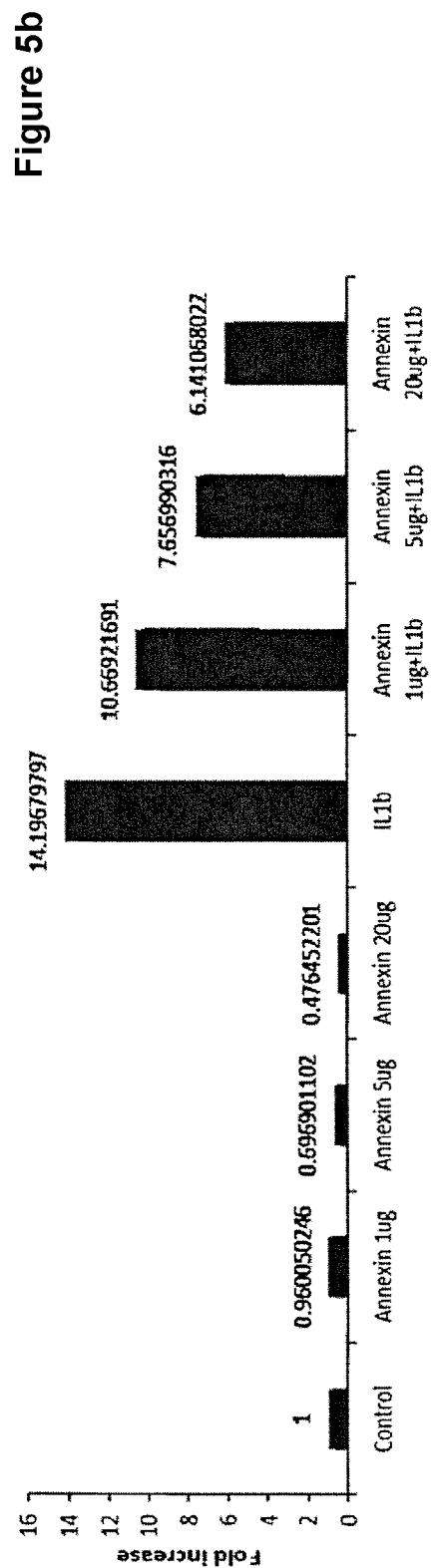

IL-6 is a pro-inflammatory biomarker associated with osteoarthritis, and COX-2 is a biomarker of joint inflammation. As shown in FIG. 5, treatment with Annexin A5 reduces the expression of both IL6 and COX2 in a dose dependent manner, when compared to cells in which an osteoarthritic state is induced using IL1-β and the control which has not been treated with IL1β. Additionally, FIG. 5 shows that treatment with Annexin A5 alone does not have an effect on IL6 or COX 2 expression.

CONCLUSIONS

The results demonstrate that treatment with Annexin A5 has a drastic impact on three major hallmarks of osteoarthritis, as it is shown to reduce osteoarthritis-associated cell death, reduce osteoarthritis biomarkers, and reduce biomarkers of osteoarthritis-associated inflammation.

In the case of osteoarthritis-associated cell death, the treatment with Annexin A5 completely rescues the phenotype, which shows that Annexin A5 exhibits the characteristics of a very effective osteoarthritis therapeutic.

Contrary to what was thought in the art, these data indicate that the presence of Annexin A5 protein in osteoarthritis joints will function to repair and/or reduce damage, rather than as a mediator of the diseases' pathogenesis. That conclusion follows from the demonstration in these experiments showing that Annexin A5 protein is able to reduce the impact of two of the important mediators of osteoarthritis disease—cell death and inflammation.

Additionally, the effectiveness of Annexin A5 in osteoarthritis model with different triggers of inflammation shows that Annexin A5 is highly likely to be therapeutically effective across a large range of different subjects.

Prophetic Example 2

The following is a prophetic example of administering Annexin A5 protein to a horse, to treat osteoarthritis.

The Annexin A5 protein used is a human recombinant Annexin A5 protein delivered as a sterile solution at 25 mg/mL. The protein solution is kept frozen during transport. Upon delivery the protein solution should be stored in the refrigerator (2-8° C.). Before sample withdrawal for dilution the protein stock solution in the vial should be gently swirled to make it homogenous.

The Annexin A5 protein is diluted to create the "vehicle". The vehicle must be stored in the refrigerator.

Three different joint pairs will be used in this study. The tiobiotarsal joints will be used for evaluation of potential vehicle effect while the radiocarpal and intercarpal joints will be used for evaluation of Annexin A5 effects. As the tiobiotarsal joint has a larger volume of synovial fluid the administered volume of vehicle will be twice compared to the volume administered to the radiocarpal/intercarpal joints in order to obtain a final concentration in the synovial fluid that is the same for two types of joints.

Two doses of ANXA5 in synovial fluid will be tested, 20 μg/mL (radiocarpal joint) and 200 μg/mL (intercarpal joint).

TABLE 1

| Treatment schedule | | | | |
|---|---|---|---|---|
| Joint | Synovial fluid volume in the joint (ml) | Treatment | Dose of ANXV5 in synovial fluid | Volume injected (% of synovial volume) |
| Tiobiotarsal | 22.5 (per joint) | Vehicle | — | 4 ml (17.8%) |
| Intercarpal | 11.5 (per joint) | Annexin A5 | 174 μg/ml | 2 ml of solution A (17.4%) |
| Radiocarpal | 11.7 (per joint) | Annexin A5 | 17 μg/ml | 2 ml of solution B (17.1%) |

It is contemplated that any use, method or composition described herein can be implemented with respect to any other use, method or composition described herein.

The use of the word "a" or "an" when used in conjunction with the term "comprising" in the claims and/or the specification may mean "one," but it is also consistent with the meaning of "one or more," "at least one," and "one or more than one."

Unless stated otherwise, the term "about" as used herein may be used herein to mean a range of ±50%, ±40%, ±30%, ±20%, ±10%, ±5%, ±4%, ±3%, ±2% or ±1% of the value mentioned.

It should be understood that the foregoing description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for the treatment of generalized nodal osteoarthritis or erosive osteoarthritis in one or more joints in a subject, comprising administering to said subject an active agent,
    wherein the active agent consists of an Annexin A5 protein or a dimer of an Annexin A5 protein;
    wherein the Annexin A5 protein consists of an amino acid sequence which is more than 95% identical to human Annexin A5 set forth in SEQ ID NO: 1, either with or without the N-terminal methionine; and
    wherein the active agent is administered to the joint or each of the joints.

2. The method according to claim 1, wherein the active agent is:
   a) a protein consisting of the sequence of human Annexin A5;
   b) a mammalian orthologue of human Annexin A5;
   c) an allelic or genetic variant of a) or b); or
   d) a protein which is 99% identical to human Annexin A5 set forth in SEQ ID NO:1, either with or without the N-terminal methionine.

3. The method according to claim 2, wherein the active agent is human Annexin A5 set forth in SEQ ID NO: 1, either with or without the N-terminal methionine.

4. The method according to claim 1, wherein the joint or each of the joints is selected from the group consisting of: a synovial joint, an amphiarthrosis joint, and a synarthrosis joint.

5. The method according to claim 4, wherein the synovial joint is one or more synovial joints selected from the group consisting of: a plane joint, a ball and socket joint, a hinge joint, a pivot joint, a condyloid joint, and a saddle joint.

6. The method according to claim 5, wherein
   the plane joint is one or more joints selected from the list consisting of: a costovertebral joint, a facet joint, a midcarpal joint, a carpometacarpal finger joint, an intermetacarpal joint, a sacroiliac joint, a zygapophyseal joint, a sternocostal joint, a subtalar joint (or a talocalcaneal joint), and an acromioclavicular joint;
   the ball and socket joint is one or more joints selected from the list consisting of: a tibiotarsal joint, a tibiofibular joint, a shoulder joint, a talocalcaneonavicular joint, and a hip joint;
   the hinge joint is one or more joints selected from the list consisting of: an ankle joint, an elbow joint, a temporomandibular joint, an interphalangeal joint, a stifle joint, and a knee joint;
   the pivot joint is one or more joints selected from the list consisting of: an atlantoaxial joint, an atlanto-axial joint, a proximal radioulnar joint, a hock joint, a tarsal joint, a talocalcaneonavicular joint, a calcaneocuboid joint, and a distal radioulnar joint;
   the condyloid joint is one or more joints selected from the list consisting of: an atlanto-occipital joint, a radiocarpal joint, a metatarsophalangeal joint, a wrist joint, an intercarpal joint, a radiocarpal joint, and a metacarpophalangeal joint; and
   the saddle joint is one or more joints selected from the list consisting of: a carpometacarpal thumb joint, a calcaneocuboid joint, and a sternoclavicular joint.

7. The method according to claim 1, wherein the subject is a mammalian subject.

8. The method according to claim 1, wherein the subject is not a juvenile and/or is a subject that has completed physical growth.

9. The method according to claim 7, wherein the subject is a human.

10. The method according to claim 9, wherein the subject is 45 or more years of age.

11. The method according to claim 7, wherein the subject is an equine, a bovine, a camel, a pig, a llama, an alpaca, a sheep, a goat, a canine, a feline, a rabbit, or a rodent.

12. The method according to claim 7, wherein the subject is a horse.

13. The method according to claim 12, wherein the subject is 5 or more years of age.

14. The method according to claim 1, wherein the active agent is administered at a concentration of at least 1 µg/ml.

15. The method according to claim 1, wherein the active agent is administered into the joint or each of the joints at a volume of 1 ml or more.

16. The method according to claim 1, wherein the active agent is administered into the joint or each of the joints at a volume of 10 ml or less.

17. The method according to claim 1, wherein the subject is treated with the active agent separately, simultaneously, or sequentially with one or more additional treatments selected from one or more of: lifestyle changes, medication, and surgery.

18. The method according to claim 1, wherein the active agent is formulated in a composition.

19. The method according to claim 18, wherein the composition is a pharmaceutically acceptable composition or a veterinarially acceptable composition.

20. The method according to claim 18, wherein the composition is administered into the joint or each of the joints at a volume of 1 ml or more.

21. The method according to claim 18, wherein the composition is administered into the joint or each of the joints at a volume of 10 ml or less.

22. The method according to claim 18, wherein the subject is treated with the composition separately, simultaneously, or sequentially with one or more additional treatments selected from one or more of: lifestyle changes, medication, and surgery.

* * * * *

SEQUENCE LISTING

<160> NUMBER OF SEQ ID NOS: 1

<210> SEQ ID NO 1
<211> LENGTH: 320
<212> TYPE: PRT
<213> ORGANISM: Homo sapiens

<400> SEQUENCE: 1

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320
```